US012605312B2

(12) United States Patent
Luo et al.

(10) Patent No.: US 12,605,312 B2
(45) Date of Patent: Apr. 21, 2026

(54) PREPARATION METHOD AND APPLICATION OF SINGLE EMULSIFIER AND DOUBLE EMULSION BASED ON DNA TRIANGULAR ORIGAMI TECHNOLOGY

(71) Applicant: Zhejiang University, Zhejiang (CN)

(72) Inventors: Zisheng Luo, Zhejiang (CN); Hao Huang, Zhejiang (CN); Li Li, Zhejiang (CN); Guangsheng Zhao, Zhejiang (CN); Gongnian Xiao, Zhejiang (CN); Xinyu Lin, Zhejiang (CN); Yanqun Xu, Zhejiang (CN)

(73) Assignee: Zhejiang University, Hangzhou (CN)

( * ) Notice: Subject to any disclaimer, the term of this patent is extended or adjusted under 35 U.S.C. 154(b) by 1003 days.

(21) Appl. No.: 17/752,477

(22) Filed: May 24, 2022

(65) Prior Publication Data

US 2023/0000733 A1     Jan. 5, 2023

(30) Foreign Application Priority Data

May 31, 2021    (CN) .......................... 202110607095.3

(51) Int. Cl.
| | |
|---|---|
| *A61K 8/06* | (2006.01) |
| *A61Q 19/02* | (2006.01) |
| *B82Y 5/00* | (2011.01) |
| *C12N 15/11* | (2006.01) |

(52) U.S. Cl.
CPC ................ *A61K 8/06* (2013.01); *A61Q 19/02* (2013.01); *C12N 15/111* (2013.01); *B82Y 5/00* (2013.01)

(58) Field of Classification Search
CPC .......... A61K 8/06; A61K 8/066; A61K 8/606; C12N 2310/3515
See application file for complete search history.

(56) References Cited

PUBLICATIONS

Ishikawa D, Suzuki Y, Kurokawa C, Ohara M, Tsuchiya M, Morita M, Yanagisawa M, Endo M, Kawano R, Takinoue M. DNA Origami Nanoplate-Based Emulsion with Nanopore Function. Angew Chem Int Ed Engl. Oct. 21, 2019;58(43):15299-15303. doi:10.1002/anie. 201908392. Epub Sep. 13, 2019. PMID: 31411794. (Year: 2019).*

* cited by examiner

*Primary Examiner* — Christopher M Babic
*Assistant Examiner* — Qinhua Gu
(74) *Attorney, Agent, or Firm* — MUNCY, GEISSLER, OLDS & LOWE, P.C.

(57) ABSTRACT

A preparation method and application of a single emulsifier and a double emulsion based on DNA triangular origami technology include designing and synthesizing staple strands of DNA triangular origami; mixing DNA scaffold strand and staple strands to synthesize the DNA triangular origami; purifying and enriching the triangular origami; and preparing the double emulsion. A process of the disclosure is simple, the obtained DNA triangular origami can be used as a single emulsifier of the double emulsion, the prepared emulsion can deliver hydrophilic arbutin and hydrophobic coumaric acid at the same time, and a central nano hole of the DNA triangular origami can be used as a nano channel for releasing arbutin and coumaric acid. Zero-order release can be achieved through an intermolecular force between arbutin and coumaric acid and the DNA triangular origami and pore confinement effect.

8 Claims, 6 Drawing Sheets

Specification includes a Sequence Listing.

Control

Embodiment 1

Comparison 1

Comparison 2

Comparison 3

SEQUENCE LISTING

<160> NUMBER OF SEQ ID NOS: 156

<210> SEQ ID NO 1
<211> LENGTH: 48
<212> TYPE: DNA
<213> ORGANISM: Artificial Sequence -continued
<220> FEATURE:
<223> OTHER INFORMATION: Synthesized

<400> SEQUENCE: 1
gcctgagtgc ataaagctaa atcgttcatt tggggcgcga tataatgc                48

<210> SEQ ID NO 2
<211> LENGTH: 48
<212> TYPE: DNA
<213> ORGANISM: Artificial Sequence
<220> FEATURE:
<223> OTHER INFORMATION: Synthesized

<400> SEQUENCE: 2
gcaaacaaga gaatcgatga acgggtagct atttttgaga aatgcaat                48

<210> SEQ ID NO 3
<211> LENGTH: 35
<212> TYPE: DNA
<213> ORGANISM: Artificial Sequence
<220> FEATURE:
<223> OTHER INFORMATION: Synthesized

<400> SEQUENCE: 3
caccctcagc cggtttatca gcttgctctc caaaa                              35

<210> SEQ ID NO 4
<211> LENGTH: 32
<212> TYPE: DNA
<213> ORGANISM: Artificial Sequence
<220> FEATURE:
<223> OTHER INFORMATION: Synthesized

<400> SEQUENCE: 4
gtaaagcctg gggtgcttta tttcaacgca ag                                 32

<210> SEQ ID NO 5
<211> LENGTH: 35
<212> TYPE: DNA
<213> ORGANISM: Artificial Sequence
<220> FEATURE:
<223> OTHER INFORMATION: Synthesized

<400> SEQUENCE: 5
aaatatcgcg taacagttca gaaaacgaca ctatc                              35

<210> SEQ ID NO 6
<211> LENGTH: 32
<212> TYPE: DNA
<213> ORGANISM: Artificial Sequence
<220> FEATURE:
<223> OTHER INFORMATION: Synthesized

<400> SEQUENCE: 6
ttagtttgcc atataacagt tgattcccaa tt                                 32

<210> SEQ ID NO 7
<211> LENGTH: 35
<212> TYPE: DNA
<213> ORGANISM: Artificial Sequence
<220> FEATURE:
<223> OTHER INFORMATION: Synthesized

<400> SEQUENCE: 7
taaatcctaa gcgtcataca tggcttttga tgata                              35

<210> SEQ ID NO 8
<211> LENGTH: 40
<212> TYPE: DNA
<213> ORGANISM: Artificial Sequence
<220> FEATURE:
<223> OTHER INFORMATION: Synthesized

<400> SEQUENCE: 8
aatcagattc ctgaatctta ccaacgctaa cgagcgtctt                          40

<210> SEQ ID NO 9
<211> LENGTH: 32
<212> TYPE: DNA
<213> ORGANISM: Artificial Sequence
<220> FEATURE:
<223> OTHER INFORMATION: Synthesized

<400> SEQUENCE: 9
ggtaatagta atcatacagg caaggcaaaa gg                                  32

<210> SEQ ID NO 10
<211> LENGTH: 35
<212> TYPE: DNA
<213> ORGANISM: Artificial Sequence
<220> FEATURE:
<223> OTHER INFORMATION: Synthesized

<400> SEQUENCE: 10
gatagcgtcc aataagaagt tttgccagat aataa                               35

<210> SEQ ID NO 11
<211> LENGTH: 35
<212> TYPE: DNA
<213> ORGANISM: Artificial Sequence
<220> FEATURE:
<223> OTHER INFORMATION: Synthesized

<400> SEQUENCE: 11
attattacga gaggcttttg caaactgcgg aatcg                               35

<210> SEQ ID NO 12
<211> LENGTH: 39
<212> TYPE: DNA
<213> ORGANISM: Artificial Sequence
<220> FEATURE:
<223> OTHER INFORMATION: Synthesized

<400> SEQUENCE: 12
cacttgaaac atgaaagtat taagaggctg agactcaag                           39

<210> SEQ ID NO 13
<211> LENGTH: 32
<212> TYPE: DNA
<213> ORGANISM: Artificial Sequence
<220> FEATURE:
<223> OTHER INFORMATION: Synthesized

<400> SEQUENCE: 13
ggtggttccg aaatcggcaa aatccagcag gc                                  32

<210> SEQ ID NO 14
<211> LENGTH: 32
<212> TYPE: DNA
<213> ORGANISM: Artificial Sequence
<220> FEATURE:
<223> OTHER INFORMATION: Synthesized -continued

<400> SEQUENCE: 14
ttaatagaag gcttatccgt cggctgtctt tc                                    32

<210> SEQ ID NO 15
<211> LENGTH: 19
<212> TYPE: DNA
<213> ORGANISM: Artificial Sequence
<220> FEATURE:
<223> OTHER INFORMATION: Synthesized

<400> SEQUENCE: 15
tcagagggcg cattagacg                                                   19

<210> SEQ ID NO 16
<211> LENGTH: 32
<212> TYPE: DNA
<213> ORGANISM: Artificial Sequence
<220> FEATURE:
<223> OTHER INFORMATION: Synthesized

<400> SEQUENCE: 16
gaattgagtg ggcgcatcgt aaccgtgcaa gc                                    32

<210> SEQ ID NO 17
<211> LENGTH: 32
<212> TYPE: DNA
<213> ORGANISM: Artificial Sequence
<220> FEATURE:
<223> OTHER INFORMATION: Synthesized

<400> SEQUENCE: 17
tcagaaccgc caccctccag tacaaactat cc                                    32

<210> SEQ ID NO 18
<211> LENGTH: 46
<212> TYPE: DNA
<213> ORGANISM: Artificial Sequence
<220> FEATURE:
<223> OTHER INFORMATION: Synthesized

<400> SEQUENCE: 18
tcataatcaa aagaggcagg tcagacgagt gtactggtaa taagtt                     46

<210> SEQ ID NO 19
<211> LENGTH: 24
<212> TYPE: DNA
<213> ORGANISM: Artificial Sequence
<220> FEATURE:
<223> OTHER INFORMATION: Synthesized

<400> SEQUENCE: 19
ctaatgagtg agctaaccac gctg                                             24

<210> SEQ ID NO 20
<211> LENGTH: 43
<212> TYPE: DNA
<213> ORGANISM: Artificial Sequence
<220> FEATURE:
<223> OTHER INFORMATION: Synthesized

<400> SEQUENCE: 20
gataaaaatt tttagatatg accctgtaat accgcaaatg gtc                        43

<210> SEQ ID NO 21

```
<211> LENGTH: 32
<212> TYPE: DNA
<213> ORGANISM: Artificial Sequence
<220> FEATURE:
<223> OTHER INFORMATION: Synthesized

<400> SEQUENCE: 21
caaaagaata taataacgga atacccaaac ac                                      32

<210> SEQ ID NO 22
<211> LENGTH: 35
<212> TYPE: DNA
<213> ORGANISM: Artificial Sequence
<220> FEATURE:
<223> OTHER INFORMATION: Synthesized

<400> SEQUENCE: 22
gcctgtttat caaagaaacc aatcaataag tattc                                   35

<210> SEQ ID NO 23
<211> LENGTH: 35
<212> TYPE: DNA
<213> ORGANISM: Artificial Sequence
<220> FEATURE:
<223> OTHER INFORMATION: Synthesized

<400> SEQUENCE: 23
ggattagcgg ggttttcag agccaccacc ctcta                                    35

<210> SEQ ID NO 24
<211> LENGTH: 32
<212> TYPE: DNA
<213> ORGANISM: Artificial Sequence
<220> FEATURE:
<223> OTHER INFORMATION: Synthesized

<400> SEQUENCE: 24
gaaagacagt tgtcacaatc aatagaaaaa tc                                      32

<210> SEQ ID NO 25
<211> LENGTH: 44
<212> TYPE: DNA
<213> ORGANISM: Artificial Sequence
<220> FEATURE:
<223> OTHER INFORMATION: Synthesized

<400> SEQUENCE: 25
ggtaacgcca gggttttccc agtctccaca caacatacga tgcg                         44

<210> SEQ ID NO 26
<211> LENGTH: 39
<212> TYPE: DNA
<213> ORGANISM: Artificial Sequence
<220> FEATURE:
<223> OTHER INFORMATION: Synthesized

<400> SEQUENCE: 26
tcataagcaa actccaacag gtcaggatta gagagtctg                               39

<210> SEQ ID NO 27
<211> LENGTH: 32
<212> TYPE: DNA
<213> ORGANISM: Artificial Sequence
<220> FEATURE:
<223> OTHER INFORMATION: Synthesized

<400> SEQUENCE: 27
```

-continued

---

```
caaggcgatt aagttgtgcc tgagagtctg ga                                    32

<210> SEQ ID NO 28
<211> LENGTH: 35
<212> TYPE: DNA
<213> ORGANISM: Artificial Sequence
<220> FEATURE:
<223> OTHER INFORMATION: Synthesized

<400> SEQUENCE: 28
aaaaccaaaa tagcaggtag aaagattcag tgaat                                 35

<210> SEQ ID NO 29
<211> LENGTH: 24
<212> TYPE: DNA
<213> ORGANISM: Artificial Sequence
<220> FEATURE:
<223> OTHER INFORMATION: Synthesized

<400> SEQUENCE: 29
ccagttacaa ataaaatta actg                                              24

<210> SEQ ID NO 30
<211> LENGTH: 32
<212> TYPE: DNA
<213> ORGANISM: Artificial Sequence
<220> FEATURE:
<223> OTHER INFORMATION: Synthesized

<400> SEQUENCE: 30
gtaggaatca ttaccgcgcc caatgtatta aa                                    32

<210> SEQ ID NO 31
<211> LENGTH: 19
<212> TYPE: DNA
<213> ORGANISM: Artificial Sequence
<220> FEATURE:
<223> OTHER INFORMATION: Synthesized

<400> SEQUENCE: 31
ccaagtacat tctgtccag                                                   19

<210> SEQ ID NO 32
<211> LENGTH: 35
<212> TYPE: DNA
<213> ORGANISM: Artificial Sequence
<220> FEATURE:
<223> OTHER INFORMATION: Synthesized

<400> SEQUENCE: 32
tttttgttta agccttaaat caagataggc gtttt                                 35

<210> SEQ ID NO 33
<211> LENGTH: 45
<212> TYPE: DNA
<213> ORGANISM: Artificial Sequence
<220> FEATURE:
<223> OTHER INFORMATION: Synthesized

<400> SEQUENCE: 33
tagaaaatac atacataaag gtggcaacat atgcgccaaa gacaa                      45

<210> SEQ ID NO 34
<211> LENGTH: 32
<212> TYPE: DNA
```

-continued

<213> ORGANISM: Artificial Sequence
<220> FEATURE:
<223> OTHER INFORMATION: Synthesized

<400> SEQUENCE: 34
tttcgtcaca gagccaccac cctcagagca tg                                   32

<210> SEQ ID NO 35
<211> LENGTH: 32
<212> TYPE: DNA
<213> ORGANISM: Artificial Sequence
<220> FEATURE:
<223> OTHER INFORMATION: Synthesized

<400> SEQUENCE: 35
gggaaggtaa atattgtcca gagcctaatt tg                                   32

<210> SEQ ID NO 36
<211> LENGTH: 35
<212> TYPE: DNA
<213> ORGANISM: Artificial Sequence
<220> FEATURE:
<223> OTHER INFORMATION: Synthesized

<400> SEQUENCE: 36
cttttcagct aatgcagaaa aattcttacc agtat                                35

<210> SEQ ID NO 37
<211> LENGTH: 35
<212> TYPE: DNA
<213> ORGANISM: Artificial Sequence
<220> FEATURE:
<223> OTHER INFORMATION: Synthesized

<400> SEQUENCE: 37
aaagccaacg ctcaacgaca ataaacaaca tgatc                                35

<210> SEQ ID NO 38
<211> LENGTH: 21
<212> TYPE: DNA
<213> ORGANISM: Artificial Sequence
<220> FEATURE:
<223> OTHER INFORMATION: Synthesized

<400> SEQUENCE: 38
gatttaggcg tttaccagac g                                               21

<210> SEQ ID NO 39
<211> LENGTH: 40
<212> TYPE: DNA
<213> ORGANISM: Artificial Sequence
<220> FEATURE:
<223> OTHER INFORMATION: Synthesized

<400> SEQUENCE: 39
cttgagatgg tttaatttca actttaatca tttcagttga                           40

<210> SEQ ID NO 40
<211> LENGTH: 32
<212> TYPE: DNA
<213> ORGANISM: Artificial Sequence
<220> FEATURE:
<223> OTHER INFORMATION: Synthesized

<400> SEQUENCE: 40
tacaattgcg aataataatt agttagcgta ac                                   32

```
<210> SEQ ID NO 41
<211> LENGTH: 35
<212> TYPE: DNA
<213> ORGANISM: Artificial Sequence
<220> FEATURE:
<223> OTHER INFORMATION: Synthesized

<400> SEQUENCE: 41
gtgtaggtaa agaattaatg ccggagaggt aatcg                                 35

<210> SEQ ID NO 42
<211> LENGTH: 42
<212> TYPE: DNA
<213> ORGANISM: Artificial Sequence
<220> FEATURE:
<223> OTHER INFORMATION: Synthesized

<400> SEQUENCE: 42
taaaactagc taaattgtaa acgttaatat tttgttaaaa tt                         42

<210> SEQ ID NO 43
<211> LENGTH: 35
<212> TYPE: DNA
<213> ORGANISM: Artificial Sequence
<220> FEATURE:
<223> OTHER INFORMATION: Synthesized

<400> SEQUENCE: 43
gatcattttc agggatagcc tcaagagaag gatta                                 35

<210> SEQ ID NO 44
<211> LENGTH: 15
<212> TYPE: DNA
<213> ORGANISM: Artificial Sequence
<220> FEATURE:
<223> OTHER INFORMATION: Synthesized

<400> SEQUENCE: 44
aggcgcatga ccaac                                                       15

<210> SEQ ID NO 45
<211> LENGTH: 32
<212> TYPE: DNA
<213> ORGANISM: Artificial Sequence
<220> FEATURE:
<223> OTHER INFORMATION: Synthesized

<400> SEQUENCE: 45
tttgaaagag gacagacatt aaacgggtaa aa                                    32

<210> SEQ ID NO 46
<211> LENGTH: 35
<212> TYPE: DNA
<213> ORGANISM: Artificial Sequence
<220> FEATURE:
<223> OTHER INFORMATION: Synthesized

<400> SEQUENCE: 46
tttcaccatt aatgaatcgg ccaatcatgg tcata                                 35

<210> SEQ ID NO 47
<211> LENGTH: 32
<212> TYPE: DNA
<213> ORGANISM: Artificial Sequence
<220> FEATURE:
```

-continued

<223> OTHER INFORMATION: Synthesized

<400> SEQUENCE: 47
tcaaaaatgc tgcgcaactg ttgggaaggc ga                                    32

<210> SEQ ID NO 48
<211> LENGTH: 32
<212> TYPE: DNA
<213> ORGANISM: Artificial Sequence
<220> FEATURE:
<223> OTHER INFORMATION: Synthesized

<400> SEQUENCE: 48
gaattacgag gcatagtaag agcaagaatg ac                                    32

<210> SEQ ID NO 49
<211> LENGTH: 35
<212> TYPE: DNA
<213> ORGANISM: Artificial Sequence
<220> FEATURE:
<223> OTHER INFORMATION: Synthesized

<400> SEQUENCE: 49
gtgagaagaa ttagcaaaat taacaattct actaa                                 35

<210> SEQ ID NO 50
<211> LENGTH: 40
<212> TYPE: DNA
<213> ORGANISM: Artificial Sequence
<220> FEATURE:
<223> OTHER INFORMATION: Synthesized

<400> SEQUENCE: 50
taaatcagct catttttgtg agcgagtaac aacccgtcgg                             40

<210> SEQ ID NO 51
<211> LENGTH: 32
<212> TYPE: DNA
<213> ORGANISM: Artificial Sequence
<220> FEATURE:
<223> OTHER INFORMATION: Synthesized

<400> SEQUENCE: 51
tcaaaaataa ttcgcgttag ccggaacgag ac                                    32

<210> SEQ ID NO 52
<211> LENGTH: 32
<212> TYPE: DNA
<213> ORGANISM: Artificial Sequence
<220> FEATURE:
<223> OTHER INFORMATION: Synthesized

<400> SEQUENCE: 52
tttaattgct ccttttgata agaggtcata gt                                    32

<210> SEQ ID NO 53
<211> LENGTH: 35
<212> TYPE: DNA
<213> ORGANISM: Artificial Sequence
<220> FEATURE:
<223> OTHER INFORMATION: Synthesized

<400> SEQUENCE: 53
cctaaaacga aagggtagca acggctacag atcgt                                 35

-continued

```
<210> SEQ ID NO 54
<211> LENGTH: 21
<212> TYPE: DNA
<213> ORGANISM: Artificial Sequence
<220> FEATURE:
<223> OTHER INFORMATION: Synthesized

<400> SEQUENCE: 54
attccaagaa cggagcaagc a                                          21

<210> SEQ ID NO 55
<211> LENGTH: 33
<212> TYPE: DNA
<213> ORGANISM: Artificial Sequence
<220> FEATURE:
<223> OTHER INFORMATION: Synthesized

<400> SEQUENCE: 55
ccataattag agccagcaaa ttcatatggt tta                             33

<210> SEQ ID NO 56
<211> LENGTH: 35
<212> TYPE: DNA
<213> ORGANISM: Artificial Sequence
<220> FEATURE:
<223> OTHER INFORMATION: Synthesized

<400> SEQUENCE: 56
cccaatagga accccacaga cagccctcat ttttc                           35

<210> SEQ ID NO 57
<211> LENGTH: 32
<212> TYPE: DNA
<213> ORGANISM: Artificial Sequence
<220> FEATURE:
<223> OTHER INFORMATION: Synthesized

<400> SEQUENCE: 57
cggttgataa tcagaaaata ttcattaccg ac                              32

<210> SEQ ID NO 58
<211> LENGTH: 44
<212> TYPE: DNA
<213> ORGANISM: Artificial Sequence
<220> FEATURE:
<223> OTHER INFORMATION: Synthesized

<400> SEQUENCE: 58
acggaaatta ttcattaaag gtgatcaagt ttgcctttag cttt                 44

<210> SEQ ID NO 59
<211> LENGTH: 48
<212> TYPE: DNA
<213> ORGANISM: Artificial Sequence
<220> FEATURE:
<223> OTHER INFORMATION: Synthesized

<400> SEQUENCE: 59
gtttgccccc ttataaatca aaagaatagc ccgagatagg agttgcag            48

<210> SEQ ID NO 60
<211> LENGTH: 33
<212> TYPE: DNA
<213> ORGANISM: Artificial Sequence
<220> FEATURE:
<223> OTHER INFORMATION: Synthesized
```

-continued

<400> SEQUENCE: 60
gctgttgcat gcctgcaggt gcgatcggtg cgg                                    33

<210> SEQ ID NO 61
<211> LENGTH: 32
<212> TYPE: DNA
<213> ORGANISM: Artificial Sequence
<220> FEATURE:
<223> OTHER INFORMATION: Synthesized

<400> SEQUENCE: 61
gaaaatcctg tttgatctgc gaacgagtag at                                     32

<210> SEQ ID NO 62
<211> LENGTH: 32
<212> TYPE: DNA
<213> ORGANISM: Artificial Sequence
<220> FEATURE:
<223> OTHER INFORMATION: Synthesized

<400> SEQUENCE: 62
ccaaaaagaa acgcaaagaa gaactggcat ga                                     32

<210> SEQ ID NO 63
<211> LENGTH: 43
<212> TYPE: DNA
<213> ORGANISM: Artificial Sequence
<220> FEATURE:
<223> OTHER INFORMATION: Synthesized

<400> SEQUENCE: 63
aatacgacgt tgtaaaacga gctggcgaaa gggggatgtg ctg                         43

<210> SEQ ID NO 64
<211> LENGTH: 35
<212> TYPE: DNA
<213> ORGANISM: Artificial Sequence
<220> FEATURE:
<223> OTHER INFORMATION: Synthesized

<400> SEQUENCE: 64
agattaagcc caataataag agcaagaaac aatca                                  35

<210> SEQ ID NO 65
<211> LENGTH: 45
<212> TYPE: DNA
<213> ORGANISM: Artificial Sequence
<220> FEATURE:
<223> OTHER INFORMATION: Synthesized

<400> SEQUENCE: 65
cagtttcagc ggagtgagaa tagatttcca gacgttagta ctcag                       45

<210> SEQ ID NO 66
<211> LENGTH: 40
<212> TYPE: DNA
<213> ORGANISM: Artificial Sequence
<220> FEATURE:
<223> OTHER INFORMATION: Synthesized

<400> SEQUENCE: 66
caagcggtct cacattaatt gcgtgccgga agcataaagt                             40

<210> SEQ ID NO 67
<211> LENGTH: 32

-continued

```
<212> TYPE: DNA
<213> ORGANISM: Artificial Sequence
<220> FEATURE:
<223> OTHER INFORMATION: Synthesized

<400> SEQUENCE: 67
accagtagca ccattacctt taattgtata gc                          32

<210> SEQ ID NO 68
<211> LENGTH: 24
<212> TYPE: DNA
<213> ORGANISM: Artificial Sequence
<220> FEATURE:
<223> OTHER INFORMATION: Synthesized

<400> SEQUENCE: 68
tcggtcatag ccccctcaaa caaa                                   24

<210> SEQ ID NO 69
<211> LENGTH: 32
<212> TYPE: DNA
<213> ORGANISM: Artificial Sequence
<220> FEATURE:
<223> OTHER INFORMATION: Synthesized

<400> SEQUENCE: 69
agtatgttag caaacgaaca ccctgaacaa ag                          32

<210> SEQ ID NO 70
<211> LENGTH: 32
<212> TYPE: DNA
<213> ORGANISM: Artificial Sequence
<220> FEATURE:
<223> OTHER INFORMATION: Synthesized

<400> SEQUENCE: 70
ccccctgcct atttcggaac ctattattcg ag                          32

<210> SEQ ID NO 71
<211> LENGTH: 38
<212> TYPE: DNA
<213> ORGANISM: Artificial Sequence
<220> FEATURE:
<223> OTHER INFORMATION: Synthesized

<400> SEQUENCE: 71
aagacttgag ccatttgggc gatagcagca ccgtacac                    38

<210> SEQ ID NO 72
<211> LENGTH: 35
<212> TYPE: DNA
<213> ORGANISM: Artificial Sequence
<220> FEATURE:
<223> OTHER INFORMATION: Synthesized

<400> SEQUENCE: 72
accaatagga acgtgtataa gcaaatatta tgtca                       35

<210> SEQ ID NO 73
<211> LENGTH: 35
<212> TYPE: DNA
<213> ORGANISM: Artificial Sequence
<220> FEATURE:
<223> OTHER INFORMATION: Synthesized

<400> SEQUENCE: 73
```

-continued

```
atcatatgta ccgttctagc tgataattca aaagg                              35

<210> SEQ ID NO 74
<211> LENGTH: 36
<212> TYPE: DNA
<213> ORGANISM: Artificial Sequence
<220> FEATURE:
<223> OTHER INFORMATION: Synthesized

<400> SEQUENCE: 74
aatatgaaat agcaatagct atcttaccga agccct                             36

<210> SEQ ID NO 75
<211> LENGTH: 24
<212> TYPE: DNA
<213> ORGANISM: Artificial Sequence
<220> FEATURE:
<223> OTHER INFORMATION: Synthesized

<400> SEQUENCE: 75
tgaacggtac gagaaacacc agaa                                          24

<210> SEQ ID NO 76
<211> LENGTH: 34
<212> TYPE: DNA
<213> ORGANISM: Artificial Sequence
<220> FEATURE:
<223> OTHER INFORMATION: Synthesized

<400> SEQUENCE: 76
atgagggctt gcagggagtt attaaacagc ttga                               34

<210> SEQ ID NO 77
<211> LENGTH: 48
<212> TYPE: DNA
<213> ORGANISM: Artificial Sequence
<220> FEATURE:
<223> OTHER INFORMATION: Synthesized

<400> SEQUENCE: 77
cagaagcaaa gcggattgca tcaaaaagat taaaaaatca ggtcttta               48

<210> SEQ ID NO 78
<211> LENGTH: 35
<212> TYPE: DNA
<213> ORGANISM: Artificial Sequence
<220> FEATURE:
<223> OTHER INFORMATION: Synthesized

<400> SEQUENCE: 78
caccggaacc gccaccagag ccgccgccag ccttg                              35

<210> SEQ ID NO 79
<211> LENGTH: 35
<212> TYPE: DNA
<213> ORGANISM: Artificial Sequence
<220> FEATURE:
<223> OTHER INFORMATION: Synthesized

<400> SEQUENCE: 79
gtaacaacat caagagtaat cttggcgcag acggt                              35

<210> SEQ ID NO 80
<211> LENGTH: 32
<212> TYPE: DNA
<213> ORGANISM: Artificial Sequence
```

-continued

<220> FEATURE:
<223> OTHER INFORMATION: Synthesized

<400> SEQUENCE: 80
gcctcaggaa gatcgccgca ttaaattttt gt                                    32

<210> SEQ ID NO 81
<211> LENGTH: 35
<212> TYPE: DNA
<213> ORGANISM: Artificial Sequence
<220> FEATURE:
<223> OTHER INFORMATION: Synthesized

<400> SEQUENCE: 81
agtaacagtg cccgtataaa cagttacgcc accag                                 35

<210> SEQ ID NO 82
<211> LENGTH: 32
<212> TYPE: DNA
<213> ORGANISM: Artificial Sequence
<220> FEATURE:
<223> OTHER INFORMATION: Synthesized

<400> SEQUENCE: 82
ctctagagga tccccggggg aggttttgaa cg                                    32

<210> SEQ ID NO 83
<211> LENGTH: 35
<212> TYPE: DNA
<213> ORGANISM: Artificial Sequence
<220> FEATURE:
<223> OTHER INFORMATION: Synthesized

<400> SEQUENCE: 83
aaaaggccaa cgcctgtagc attcatgtac cgtaa                                 35

<210> SEQ ID NO 84
<211> LENGTH: 32
<212> TYPE: DNA
<213> ORGANISM: Artificial Sequence
<220> FEATURE:
<223> OTHER INFORMATION: Synthesized

<400> SEQUENCE: 84
aagaaaaatt gcgtattggg cgccagggtg gg                                    32

<210> SEQ ID NO 85
<211> LENGTH: 35
<212> TYPE: DNA
<213> ORGANISM: Artificial Sequence
<220> FEATURE:
<223> OTHER INFORMATION: Synthesized

<400> SEQUENCE: 85
ggagatttgt atcatcgcct gataaattgt gtcat                                 35

<210> SEQ ID NO 86
<211> LENGTH: 36
<212> TYPE: DNA
<213> ORGANISM: Artificial Sequence
<220> FEATURE:
<223> OTHER INFORMATION: Synthesized

<400> SEQUENCE: 86
gccttcctgt agccagcttt catcaacatt aaatta                                36

-continued

```
<210> SEQ ID NO 87
<211> LENGTH: 35
<212> TYPE: DNA
<213> ORGANISM: Artificial Sequence
<220> FEATURE:
<223> OTHER INFORMATION: Synthesized

<400> SEQUENCE: 87
aataagacat aaaaacaggg aagtaattga gcgct                              35

<210> SEQ ID NO 88
<211> LENGTH: 35
<212> TYPE: DNA
<213> ORGANISM: Artificial Sequence
<220> FEATURE:
<223> OTHER INFORMATION: Synthesized

<400> SEQUENCE: 88
aaccacctcc ctcagagccg ccatcaccaa tgaaa                              35

<210> SEQ ID NO 89
<211> LENGTH: 32
<212> TYPE: DNA
<213> ORGANISM: Artificial Sequence
<220> FEATURE:
<223> OTHER INFORMATION: Synthesized

<400> SEQUENCE: 89
ccggagacag tcaaatcaaa aatctacgtg gg                                 32

<210> SEQ ID NO 90
<211> LENGTH: 35
<212> TYPE: DNA
<213> ORGANISM: Artificial Sequence
<220> FEATURE:
<223> OTHER INFORMATION: Synthesized

<400> SEQUENCE: 90
caatcgaaat ccgcgacctg ctccatgtta ctctg                              35

<210> SEQ ID NO 91
<211> LENGTH: 32
<212> TYPE: DNA
<213> ORGANISM: Artificial Sequence
<220> FEATURE:
<223> OTHER INFORMATION: Synthesized

<400> SEQUENCE: 91
gttttcatcg gcatttcgtt tttattttca tc                                 32

<210> SEQ ID NO 92
<211> LENGTH: 35
<212> TYPE: DNA
<213> ORGANISM: Artificial Sequence
<220> FEATURE:
<223> OTHER INFORMATION: Synthesized

<400> SEQUENCE: 92
acgttgaaaa tttcgaggtg aatttcaagg ccgct                              35

<210> SEQ ID NO 93
<211> LENGTH: 40
<212> TYPE: DNA
<213> ORGANISM: Artificial Sequence
<220> FEATURE:
<223> OTHER INFORMATION: Synthesized
```

-continued

```
<400> SEQUENCE: 93
actaaaggcg atagttgcgc cgacaatgac aacaaccatc                          40

<210> SEQ ID NO 94
<211> LENGTH: 32
<212> TYPE: DNA
<213> ORGANISM: Artificial Sequence
<220> FEATURE:
<223> OTHER INFORMATION: Synthesized

<400> SEQUENCE: 94
cgaaaaaccg tctatcacat aattactaga ac                                  32

<210> SEQ ID NO 95
<211> LENGTH: 35
<212> TYPE: DNA
<213> ORGANISM: Artificial Sequence
<220> FEATURE:
<223> OTHER INFORMATION: Synthesized

<400> SEQUENCE: 95
ggaaccagag catcagtagc gacagaaatt atcac                               35

<210> SEQ ID NO 96
<211> LENGTH: 35
<212> TYPE: DNA
<213> ORGANISM: Artificial Sequence
<220> FEATURE:
<223> OTHER INFORMATION: Synthesized

<400> SEQUENCE: 96
aaccgccacc cgctcagtac caggcggata agtgc                               35

<210> SEQ ID NO 97
<211> LENGTH: 32
<212> TYPE: DNA
<213> ORGANISM: Artificial Sequence
<220> FEATURE:
<223> OTHER INFORMATION: Synthesized

<400> SEQUENCE: 97
agtctctgaa tttaccgttc cagtcattaa ag                                  32

<210> SEQ ID NO 98
<211> LENGTH: 35
<212> TYPE: DNA
<213> ORGANISM: Artificial Sequence
<220> FEATURE:
<223> OTHER INFORMATION: Synthesized

<400> SEQUENCE: 98
taaagaacgt ggactccaac gtcaaaggtt tttct                               35

<210> SEQ ID NO 99
<211> LENGTH: 48
<212> TYPE: DNA
<213> ORGANISM: Artificial Sequence
<220> FEATURE:
<223> OTHER INFORMATION: Synthesized

<400> SEQUENCE: 99
gagaatataa agtacccaac gccaacatgt aatttaggca gaggcatt                 48

<210> SEQ ID NO 100
```

```
<211> LENGTH: 32
<212> TYPE: DNA
<213> ORGANISM: Artificial Sequence
<220> FEATURE:
<223> OTHER INFORMATION: Synthesized

<400> SEQUENCE: 100
ccagaatgga aagcgcttcg agccagtaat aa                                      32

<210> SEQ ID NO 101
<211> LENGTH: 32
<212> TYPE: DNA
<213> ORGANISM: Artificial Sequence
<220> FEATURE:
<223> OTHER INFORMATION: Synthesized

<400> SEQUENCE: 101
tacataacgc caaaaggcta aacaactttc aa                                      32

<210> SEQ ID NO 102
<211> LENGTH: 43
<212> TYPE: DNA
<213> ORGANISM: Artificial Sequence
<220> FEATURE:
<223> OTHER INFORMATION: Synthesized

<400> SEQUENCE: 102
cgtcgagacc tcagaaccgc caccaatgaa ttttcgggat ttt                         43

<210> SEQ ID NO 103
<211> LENGTH: 38
<212> TYPE: DNA
<213> ORGANISM: Artificial Sequence
<220> FEATURE:
<223> OTHER INFORMATION: Synthesized

<400> SEQUENCE: 103
gccacggcca gtgccaagct ttcctgtgtg aaattctg                               38

<210> SEQ ID NO 104
<211> LENGTH: 35
<212> TYPE: DNA
<213> ORGANISM: Artificial Sequence
<220> FEATURE:
<223> OTHER INFORMATION: Synthesized

<400> SEQUENCE: 104
ttacgaacaa agttaccaga aggaaaccga ggaaa                                  35

<210> SEQ ID NO 105
<211> LENGTH: 35
<212> TYPE: DNA
<213> ORGANISM: Artificial Sequence
<220> FEATURE:
<223> OTHER INFORMATION: Synthesized

<400> SEQUENCE: 105
ctcactgccc gccgcctggc cctgagaggt tgagt                                  35

<210> SEQ ID NO 106
<211> LENGTH: 32
<212> TYPE: DNA
<213> ORGANISM: Artificial Sequence
<220> FEATURE:
<223> OTHER INFORMATION: Synthesized

<400> SEQUENCE: 106
```
aagaaccgga gccccaaaaa caggaagatc ca                                    32

<210> SEQ ID NO 107
<211> LENGTH: 29
<212> TYPE: DNA
<213> ORGANISM: Artificial Sequence
<220> FEATURE:
<223> OTHER INFORMATION: Synthesized

<400> SEQUENCE: 107
atattgttgt accaaaaaca taccctcat                                        29

<210> SEQ ID NO 108
<211> LENGTH: 32
<212> TYPE: DNA
<213> ORGANISM: Artificial Sequence
<220> FEATURE:
<223> OTHER INFORMATION: Synthesized

<400> SEQUENCE: 108
ccgacttgcg taccgagctc gaattcgtaa cg                                    32

<210> SEQ ID NO 109
<211> LENGTH: 32
<212> TYPE: DNA
<213> ORGANISM: Artificial Sequence
<220> FEATURE:
<223> OTHER INFORMATION: Synthesized

<400> SEQUENCE: 109
atattttaga tctacaaagg ctatcaggtc at                                    32

<210> SEQ ID NO 110
<211> LENGTH: 40
<212> TYPE: DNA
<213> ORGANISM: Artificial Sequence
<220> FEATURE:
<223> OTHER INFORMATION: Synthesized

<400> SEQUENCE: 110
ttttaagaaa agtaagcaga tagcagactc cttattacgc                            40

<210> SEQ ID NO 111
<211> LENGTH: 48
<212> TYPE: DNA
<213> ORGANISM: Artificial Sequence
<220> FEATURE:
<223> OTHER INFORMATION: Synthesized

<400> SEQUENCE: 111
ggtttagtac cgccacgggt tgatataagt atagcccgga ataggtgt                   48

<210> SEQ ID NO 112
<211> LENGTH: 35
<212> TYPE: DNA
<213> ORGANISM: Artificial Sequence
<220> FEATURE:
<223> OTHER INFORMATION: Synthesized

<400> SEQUENCE: 112
tgtagctcaa catgttttaa atatcctgtt tagct                                 35

<210> SEQ ID NO 113
<211> LENGTH: 32
<212> TYPE: DNA

<213> ORGANISM: Artificial Sequence
<220> FEATURE:
<223> OTHER INFORMATION: Synthesized

<400> SEQUENCE: 113
gccattcgcc attcaggaaa atagcagccc aa                                         32

<210> SEQ ID NO 114
<211> LENGTH: 35
<212> TYPE: DNA
<213> ORGANISM: Artificial Sequence
<220> FEATURE:
<223> OTHER INFORMATION: Synthesized

<400> SEQUENCE: 114
tcattcagtg gattttaaga actggccgga acaac                                      35

<210> SEQ ID NO 115
<211> LENGTH: 32
<212> TYPE: DNA
<213> ORGANISM: Artificial Sequence
<220> FEATURE:
<223> OTHER INFORMATION: Synthesized

<400> SEQUENCE: 115
agcattaaca tccaataaaa atgtttagaa cc                                         32

<210> SEQ ID NO 116
<211> LENGTH: 35
<212> TYPE: DNA
<213> ORGANISM: Artificial Sequence
<220> FEATURE:
<223> OTHER INFORMATION: Synthesized

<400> SEQUENCE: 116
aagcgaacca gaccggaaat attcattgaa tcata                                      35

<210> SEQ ID NO 117
<211> LENGTH: 32
<212> TYPE: DNA
<213> ORGANISM: Artificial Sequence
<220> FEATURE:
<223> OTHER INFORMATION: Synthesized

<400> SEQUENCE: 117
gtaaagtacg cactcatcga gaacaagcaa gc                                         32

<210> SEQ ID NO 118
<211> LENGTH: 45
<212> TYPE: DNA
<213> ORGANISM: Artificial Sequence
<220> FEATURE:
<223> OTHER INFORMATION: Synthesized

<400> SEQUENCE: 118
aataagcaac taaagtacgg tgtctggaag tttcattacc attag                           45

<210> SEQ ID NO 119
<211> LENGTH: 32
<212> TYPE: DNA
<213> ORGANISM: Artificial Sequence
<220> FEATURE:
<223> OTHER INFORMATION: Synthesized

<400> SEQUENCE: 119
gccgccggaa accaggcaat ctgccagttt ga                                         32

```
<210> SEQ ID NO 120
<211> LENGTH: 32
<212> TYPE: DNA
<213> ORGANISM: Artificial Sequence
<220> FEATURE:
<223> OTHER INFORMATION: Synthesized

<400> SEQUENCE: 120
cacggaataa gtttattcat cggaacgaga gg                               32

<210> SEQ ID NO 121
<211> LENGTH: 32
<212> TYPE: DNA
<213> ORGANISM: Artificial Sequence
<220> FEATURE:
<223> OTHER INFORMATION: Synthesized

<400> SEQUENCE: 121
cgagtagtaa attggggccc acgcataacc ga                               32

<210> SEQ ID NO 122
<211> LENGTH: 35
<212> TYPE: DNA
<213> ORGANISM: Artificial Sequence
<220> FEATURE:
<223> OTHER INFORMATION: Synthesized

<400> SEQUENCE: 122
aacgaactaa tcattatacc agtcagcaaa tcaac                            35

<210> SEQ ID NO 123
<211> LENGTH: 35
<212> TYPE: DNA
<213> ORGANISM: Artificial Sequence
<220> FEATURE:
<223> OTHER INFORMATION: Synthesized

<400> SEQUENCE: 123
taccttatgc aataaggctt gccctggtac agacc                            35

<210> SEQ ID NO 124
<211> LENGTH: 35
<212> TYPE: DNA
<213> ORGANISM: Artificial Sequence
<220> FEATURE:
<223> OTHER INFORMATION: Synthesized

<400> SEQUENCE: 124
acgcccctca aatgctttat ttaattcgag cttca                            35

<210> SEQ ID NO 125
<211> LENGTH: 32
<212> TYPE: DNA
<213> ORGANISM: Artificial Sequence
<220> FEATURE:
<223> OTHER INFORMATION: Synthesized

<400> SEQUENCE: 125
ataaccctaa taccacattc aactaatgca ga                               32

<210> SEQ ID NO 126
<211> LENGTH: 35
<212> TYPE: DNA
<213> ORGANISM: Artificial Sequence
<220> FEATURE:
```

-continued

<223> OTHER INFORMATION: Synthesized

<400> SEQUENCE: 126
aagggaaccg aactaggctg gctgacctta gctgc                          35

<210> SEQ ID NO 127
<211> LENGTH: 32
<212> TYPE: DNA
<213> ORGANISM: Artificial Sequence
<220> FEATURE:
<223> OTHER INFORMATION: Synthesized

<400> SEQUENCE: 127
aaaaggagcc attagcaagg ccggaaacgc cc                             32

<210> SEQ ID NO 128
<211> LENGTH: 45
<212> TYPE: DNA
<213> ORGANISM: Artificial Sequence
<220> FEATURE:
<223> OTHER INFORMATION: Synthesized

<400> SEQUENCE: 128
acgacagtag ggcttaattg agaatcgcca tatttaagac aaaag              45

<210> SEQ ID NO 129
<211> LENGTH: 35
<212> TYPE: DNA
<213> ORGANISM: Artificial Sequence
<220> FEATURE:
<223> OTHER INFORMATION: Synthesized

<400> SEQUENCE: 129
tcgtgccagc tgcagtgaga cgggcaacac actat                          35

<210> SEQ ID NO 130
<211> LENGTH: 35
<212> TYPE: DNA
<213> ORGANISM: Artificial Sequence
<220> FEATURE:
<223> OTHER INFORMATION: Synthesized

<400> SEQUENCE: 130
gttgttccag tttggaacaa gagtcgctga ttgcc                          35

<210> SEQ ID NO 131
<211> LENGTH: 40
<212> TYPE: DNA
<213> ORGANISM: Artificial Sequence
<220> FEATURE:
<223> OTHER INFORMATION: Synthesized

<400> SEQUENCE: 131
attctccgtg ggaacaaacg gcgggacgac gacagtatcg                     40

<210> SEQ ID NO 132
<211> LENGTH: 39
<212> TYPE: DNA
<213> ORGANISM: Artificial Sequence
<220> FEATURE:
<223> OTHER INFORMATION: Synthesized

<400> SEQUENCE: 132
cctgaaaaag cctgtttagt atcatatgcg ttataccgc                      39

-continued

```
<210> SEQ ID NO 133
<211> LENGTH: 35
<212> TYPE: DNA
<213> ORGANISM: Artificial Sequence
<220> FEATURE:
<223> OTHER INFORMATION: Synthesized

<400> SEQUENCE: 133
ttaacggggt cagtgcattg acaggaggtt tcacc                              35

<210> SEQ ID NO 134
<211> LENGTH: 35
<212> TYPE: DNA
<213> ORGANISM: Artificial Sequence
<220> FEATURE:
<223> OTHER INFORMATION: Synthesized

<400> SEQUENCE: 134
cgcaacacta aaacactcat ctttgacccc cacaa                              35

<210> SEQ ID NO 135
<211> LENGTH: 35
<212> TYPE: DNA
<213> ORGANISM: Artificial Sequence
<220> FEATURE:
<223> OTHER INFORMATION: Synthesized

<400> SEQUENCE: 135
tttgcgggag gctttgagga ctagccacta cgaag                              35

<210> SEQ ID NO 136
<211> LENGTH: 33
<212> TYPE: DNA
<213> ORGANISM: Artificial Sequence
<220> FEATURE:
<223> OTHER INFORMATION: Synthesized

<400> SEQUENCE: 136 tagttttttgc ggatggctta gagcttaatt gct                              33

<210> SEQ ID NO 137
<211> LENGTH: 32
<212> TYPE: DNA
<213> ORGANISM: Artificial Sequence
<220> FEATURE:
<223> OTHER INFORMATION: Synthesized

<400> SEQUENCE: 137
cgcggggaga ggcggttaat atcccatccc tc                                32

<210> SEQ ID NO 138
<211> LENGTH: 35
<212> TYPE: DNA
<213> ORGANISM: Artificial Sequence
<220> FEATURE:
<223> OTHER INFORMATION: Synthesized

<400> SEQUENCE: 138
taagaacgcg tagttgctat tttgcaccca atcca                             35

<210> SEQ ID NO 139
<211> LENGTH: 21
<212> TYPE: DNA
<213> ORGANISM: Artificial Sequence
<220> FEATURE:
<223> OTHER INFORMATION: Synthesized
```

-continued

```
<400> SEQUENCE: 139
aagttttgtc gtcaaggaac a                                                   21

<210> SEQ ID NO 140
<211> LENGTH: 35
<212> TYPE: DNA
<213> ORGANISM: Artificial Sequence
<220> FEATURE:
<223> OTHER INFORMATION: Synthesized

<400> SEQUENCE: 140
cttcactttc cagtcgggaa acgttatccg ctcac                                    35

<210> SEQ ID NO 141
<211> LENGTH: 32
<212> TYPE: DNA
<213> ORGANISM: Artificial Sequence
<220> FEATURE:
<223> OTHER INFORMATION: Synthesized

<400> SEQUENCE: 141
cgtcaccggg cgacattcaa ccgattgagg ga                                       32

<210> SEQ ID NO 142
<211> LENGTH: 24
<212> TYPE: DNA
<213> ORGANISM: Artificial Sequence
<220> FEATURE:
<223> OTHER INFORMATION: Synthesized

<400> SEQUENCE: 142
atacattttt ttgcgggaga agcc                                                24

<210> SEQ ID NO 143
<211> LENGTH: 19
<212> TYPE: DNA
<213> ORGANISM: Artificial Sequence
<220> FEATURE:
<223> OTHER INFORMATION: Synthesized

<400> SEQUENCE: 143
tacgtaataa gactttttc                                                      19

<210> SEQ ID NO 144
<211> LENGTH: 29
<212> TYPE: DNA
<213> ORGANISM: Artificial Sequence
<220> FEATURE:
<223> OTHER INFORMATION: Synthesized

<400> SEQUENCE: 144
cataaatcag aggaagcccg aaagacttc                                           29

<210> SEQ ID NO 145
<211> LENGTH: 32
<212> TYPE: DNA
<213> ORGANISM: Artificial Sequence
<220> FEATURE:
<223> OTHER INFORMATION: Synthesized

<400> SEQUENCE: 145
gttgggaaga ccatcaatat gatattcaac cc                                       32

<210> SEQ ID NO 146
<211> LENGTH: 32
```

-continued

```
<212> TYPE: DNA
<213> ORGANISM: Artificial Sequence
<220> FEATURE:
<223> OTHER INFORMATION: Synthesized

<400> SEQUENCE: 146
ccctgactat tatagtatca ccgtactcag ga                                    32

<210> SEQ ID NO 147
<211> LENGTH: 34
<212> TYPE: DNA
<213> ORGANISM: Artificial Sequence
<220> FEATURE:
<223> OTHER INFORMATION: Synthesized

<400> SEQUENCE: 147
ggagacagcc atattattta tcccagctac aatt                                  34

<210> SEQ ID NO 148
<211> LENGTH: 35
<212> TYPE: DNA
<213> ORGANISM: Artificial Sequence
<220> FEATURE:
<223> OTHER INFORMATION: Synthesized

<400> SEQUENCE: 148
gagagataac ccatttacag agagaataaa acgat                                 35

<210> SEQ ID NO 149
<211> LENGTH: 24
<212> TYPE: DNA
<213> ORGANISM: Artificial Sequence
<220> FEATURE:
<223> OTHER INFORMATION: Synthesized

<400> SEQUENCE: 149
tttgccatcg tcagactgta gcgc                                             24

<210> SEQ ID NO 150
<211> LENGTH: 36
<212> TYPE: DNA
<213> ORGANISM: Artificial Sequence
<220> FEATURE:
<223> OTHER INFORMATION: Synthesized

<400> SEQUENCE: 150
gcacgcgatt ataccaagcg cgaaacaaag tacaac                                36

<210> SEQ ID NO 151
<211> LENGTH: 45
<212> TYPE: DNA
<213> ORGANISM: Artificial Sequence
<220> FEATURE:
<223> OTHER INFORMATION: Synthesized

<400> SEQUENCE: 151
actccagcca gctttccggc accgcttctg gttcttcgct attac                      45

<210> SEQ ID NO 152
<211> LENGTH: 35
<212> TYPE: DNA
<213> ORGANISM: Artificial Sequence
<220> FEATURE:
<223> OTHER INFORMATION: Synthesized

<400> SEQUENCE: 152
```

-continued

```
gggattgacc gtaatgggat aggtcacgtt ggtgt                                35

<210> SEQ ID NO 153
<211> LENGTH: 38
<212> TYPE: DNA
<213> ORGANISM: Artificial Sequence
<220> FEATURE:
<223> OTHER INFORMATION: Synthesized

<400> SEQUENCE: 153
gaagctgaaa aggtggcatg caataaagcc tcagaaat                             38

<210> SEQ ID NO 154
<211> LENGTH: 24
<212> TYPE: DNA
<213> ORGANISM: Artificial Sequence
<220> FEATURE:
<223> OTHER INFORMATION: Synthesized

<400> SEQUENCE: 154
tatattcggt cgctgagaag tttc                                           24

<210> SEQ ID NO 155
<211> LENGTH: 35
<212> TYPE: DNA
<213> ORGANISM: Artificial Sequence
<220> FEATURE:
<223> OTHER INFORMATION: Synthesized

<400> SEQUENCE: 155
agcgaactaa tttacgagca tgtcaataga taagt                               35

<210> SEQ ID NO 156
<211> LENGTH: 29
<212> TYPE: DNA
<213> ORGANISM: Artificial Sequence
<220> FEATURE:
<223> OTHER INFORMATION: Synthesized

<400> SEQUENCE: 156
caggattggc cttgatattc atattagcg                                      29
```

PREPARATION METHOD AND APPLICATION OF SINGLE EMULSIFIER AND DOUBLE EMULSION BASED ON DNA TRIANGULAR ORIGAMI TECHNOLOGY

The instant application contains a Sequence Listing which has been submitted electronically in the ASCII text file and is hereby incorporated by reference in its entirety. The ASCII text file is a sequence listing entitled "2022-08-15-Substitute-Seq-Listing" created on Aug. 15, 2022 and having a size of 29,086 bytes in compliance of 37 CFR 1.821.

TECHNICAL FIELD

The disclosure relates to a technical field of DNA nanostructure preparation, in particular to a single emulsifier stabilized double emulsion based on DNA triangular origami technology and application of the double emulsion as a phenolic substance delivery system.

BACKGROUND ART

Structural characteristics of DNA is predictable with Watson-Crick base complementary pairing principle. In 1982, Seeman proposed to use DNA as building materials to assemble geometric objects with nanoscale features. This revolutionary idea laid foundation for a new research field, which is now called "structured DNA nanotechnology". A rigid branched DNA pattern was developed based on complementary Watson-Crick base pairs between fragments of a given oligonucleotide group by using self-identification characteristics of DNA. In 2006, Rothemund introduced scaffold-based DNA origami technologies, which makes an extraordinary breakthrough in construction of nano-scale DNA objects.

Invention of DNA origami technology is a milestone of DNA nanotechnology, in which long single-stranded DNA (ssDNA) is folded into a specified shape with assistance of hundreds of short DNA strands. Therefore, the DNA origami technology provides ability to generate nano-objects with complex shapes and complete molecular addressability in a predefined size, which makes DNA origami an important tool for constructing DNA-based nanostructures.

An emulsion is a mixture of two or more liquids, which are usually immiscible due to liquid-liquid phase separation. In the emulsion, one liquid (a dispersed phase) is dispersed in another liquid (continuous phase). Two liquids can form different types of emulsions. For example, oil and water can firstly form an oil-in-water emulsion, where oil is the dispersed phase and water is the continuous phase. Secondly, they can form water-in-oil emulsion, in which water is the dispersed phase and oil is the continuous phase. A variety of emulsions are also possible, including "water-in-oil-in-water" (W/O/W) and "oil-in-water-in-oil" (O/W/O) emulsions. The emulsion is widely used in fields of food, cosmetics and medicines for its excellent loading capacity.

A double emulsion has attracted much attention because it can be embedded with both water-phase substances and oil-phase substances. The double emulsion refers to a complex liquid dispersion system of "emulsion being dispersed in emulsion", in which droplets of a dispersed phase itself contain smaller dispersed droplets, for example, W/O/W and O/W/O emulsions. Because of its internal partition structure, the double emulsion has more advantages than a common emulsion in controlled release, active substance protection and catalysis. Although it has some advantages over a common single emulsion, a stable double emulsion is usually not formed by single emulsifiers and it is necessary to use hydrophilic and hydrophobic emulsifiers to prepare the double emulsion. For example, in preparing a W/O/W emulsion, firstly, a hydrophobic emulsifier (with hydrophilic-lipophilic balance (HLB) value of 3-8) is used to prepare a primary W/O emulsion, and then the prepared emulsion is further dispersed in an external water phase containing a hydrophilic emulsifier (HLB=9-10) to form a W/O/W double emulsion. Due to a fact that curvatures of two types of interfaces in the double emulsion are opposite and it is difficult for a single emulsifier to stabilize the two types of interfaces at the same time, it is extremely difficult to stabilize the double emulsion with one emulsifier.

Arbutin and coumaric acid both are phenolic substances, and both have anti-melanin effect, so they have whitening effect. However, arbutin is a hydrophilic substance while coumaric acid is a hydrophobic substance, and their simultaneous application is challenging. In addition, in order to ensure optimal efficacy of arbutin and coumaric acid, it is necessary to maintain their concentration, and thus it is necessary to achieve simultaneous delivery and controlled release of arbutin and coumaric acid.

SUMMARY

An object of the disclosure is to provide a single emulsifier based on a novel DNA triangular origami technology.

Another object of the present disclosure is to provide a preparation method of a double emulsion stabilized with the single emulsifier, which realizes stabilization of the double emulsion by using single component DNA triangular origami as an emulsifier, which can deliver arbutin and coumaric acid at the same time and realize controlled release to ensure that arbutin and coumaric acid provide optimal whitening effect.

A third object of the present disclosure is to provide application of the double emulsion based on DNA origami technology as a phenolic delivery system.

In order to achieve the above object, the disclosure adopts following technical schemes.

In an aspect of the disclosure, a single emulsifier based on DNA triangular origami technology is provided. The single emulsifier is DNA triangular origami prepared by modifying cholesterol onto DNA staple strands and synthesizing with a DNA scaffold strand. The cholesterol is modified onto 3' ends of the DNA staple strands, and the DNA triangular origami has a central nano hole, both of the DNA triangular origami and the central nano hole are equilateral triangles, and a number of cholesterol-modified DNA staple strands in each block unit of the DNA triangular origami is 15.

In this technical scheme, the inventor found through experiments that, with directed design of amphiphilic DNA triangular origami, a proportion of cholesterol modification has influence on emulsifying performance. The number of the cholesterol-modified DNA staple strands in each block unit is 15, which has optimal stabilizing effect on the emulsion.

As a preferred scheme of the present disclosure, the cholesterol-modified DNA staple strands are SEQ ID NO.2, SEQ ID NO.5, SEQ ID NO.6, SEQ ID NO.10, SEQ ID NO.13, SEQ ID NO.18, SEQ ID NO.19, SEQ ID NO.20, SEQ ID NO.24, SEQ ID NO.31, SEQ ID NO.36, SEQ ID NO.43, SEQ ID NO.47, SEQ ID NO.54, SEQ ID NO.57, SEQ ID NO.62, SEQ ID NO.63, SEQ ID NO.65, SEQ ID NO.66, SEQ ID NO.67, SEQ ID NO.68, SEQ ID NO.72, SEQ ID NO.77, SEQ ID NO.78, SEQ ID NO.82, SEQ ID NO.83, SEQ ID NO.87, SEQ ID NO.97, SEQ ID NO.99, SEQ ID NO.105, SEQ ID NO.111, SEQ ID NO.112, SEQ ID NO.116, SEQ ID NO.119, SEQ ID NO.126, SEQ ID NO.129, SEQ ID NO.135, SEQ ID NO.136, SEQ ID NO.139, SEQ ID NO.141, SEQ ID NO.142, SEQ ID NO.145, SEQ ID NO.149 and SEQ ID NO.155.

In another aspect of the disclosure, a preparation method of a double emulsion based on DNA triangular origami technology is provided, which includes following steps.

In Step (1), the DNA staple strands are designed and synthesized.

In Step (2), the DNA scaffold strand and the DNA staple strands are mixed and dissolved in a buffer, and a temperature program is set to synthesize the DNA triangular origami.

In Step (3), the DNA triangular origami obtained in step (2) is purified and enriched.

In Step (4), arbutin is added into an internal water phase, coumaric acid is added into an internal oil phase, the enriched DNA triangular origami obtained in step (3) is added into the internal water phase, which then is added into the internal oil phase and subjected to ultrasonic reaction to obtain a W/O emulsion.

In Step (5), the enriched DNA triangular origami obtained in step (3) is added into an external water phase, and then the W/O emulsion obtained in step (4) is added for ultrasonic reaction to prepare a W/O/W double emulsion based on the DNA triangular origami technology.

In this technical scheme, hydrophilicity of DNA itself and lipophilicity brought by cholesterol modification are used to design amphiphilic DNA triangular origami in this disclosure. Different from a traditional W/O/W double emulsion, this double emulsion is stabilized with single-component DNA triangular origami as an emulsifier, with the central nano hole of the DNA triangular origami as a nano channel for release of arbutin and coumaric acid, which realizes controlled release of arbutin and coumaric acid and has great application potential.

As a preferred scheme of the present disclosure, in step 1), a total number of the staple strands of the DNA triangular origami is 156.

As a preferred scheme of the disclosure, in step 2), the DNA scaffold strand is M13mp18, a molar concentration ratio of the DNA scaffold strand to the DNA staple strands is 1:10, and the buffer is a TAE-Mg2+ buffer. The temperature program is set to be 95° C. for 3 min, followed by temperature drops from 95° C. to 15° C. at a cooling rate of 0.01-0.02° C./s.

As a preferred scheme of the disclosure, in step 3), a concentration of the enriched DNA triangular origami is 10±1 µM.

As a preferred scheme of the disclosure, in step 4), addition amount of arbutin is 500±1 µg/mL and addition amount of coumaric acid is 100±1 µg/mL.

As a preferred scheme of the disclosure, in step 4), a volume ratio of the internal water phase to the internal oil phase is 1:4 to 6. In step 5), a volume ratio of the W/O emulsion to the external water phase is 1:4 to 6.

As a preferred scheme of the disclosure, in step 4) and step 5), ultrasonic power of the ultrasonic reaction is 80±5 W, with a frequency of 25±5 kHz and an ultrasonic duration of 90±5 s.

In a third aspect of the present disclosure, an application of a double emulsion based on DNA triangular origami technology in a phenolic delivery system is provided.

Compared with the prior art, the invention provides the following beneficial effects.

(1) In the disclosure, caDNAno software is adopted to design the DNA triangular origami, which is simple, convenient and quick to operate.

(2) In the disclosure, the cholesterol is used to modify a specific number of DNA staple strands, and the prepared DNA triangular origami can be used as a single emulsifier to stabilize the W/O/W double emulsion, which has good stability and can simultaneously deliver hydrophilic arbutin and hydrophobic coumaric acid.

(3) The DNA triangular origami designed in the disclosure has the central nano hole, which can be used as a nano channel for release of arbutin and coumaric acid, thus controlling release of arbutin and coumaric acid, and having important significance in sufficiently achieving whitening effect of arbutin and coumaric acid.

DETAILED DESCRIPTION

The disclosure will be further explained with reference to following embodiments. Experimental methods used in the following embodiments are conventional methods unless otherwise specified. Materials and reagents used in the embodiments can be available from commercial sources unless otherwise specified.

DNA scaffold strand M13mp18 was purchased from New England Biolabs Inc., USA; DNA staple strands were purchased from Shanghai Shenggong Biological Co., Ltd.; arbutin and coumaric acid were purchased from Shanghai Aladdin Biochemical Technology Co., Ltd.; a 100 kDa ultrafiltration tube was purchased from Millipore Inc., USA; PTC-200 PCR instrument is from MJ Research Inc., Canada; Dimension Icon atomic force microscope is from Bruker Inc., Germany; OCA-20 contact angle tester is from Dataphysics Inc., Germany; Turbiscan Lab Expert stability analyzer is from Formulaction Inc., France; and Agilent 1290 Ultra Performance Liquid Chromatography is from Agilent Inc., USA.

Figure 1:
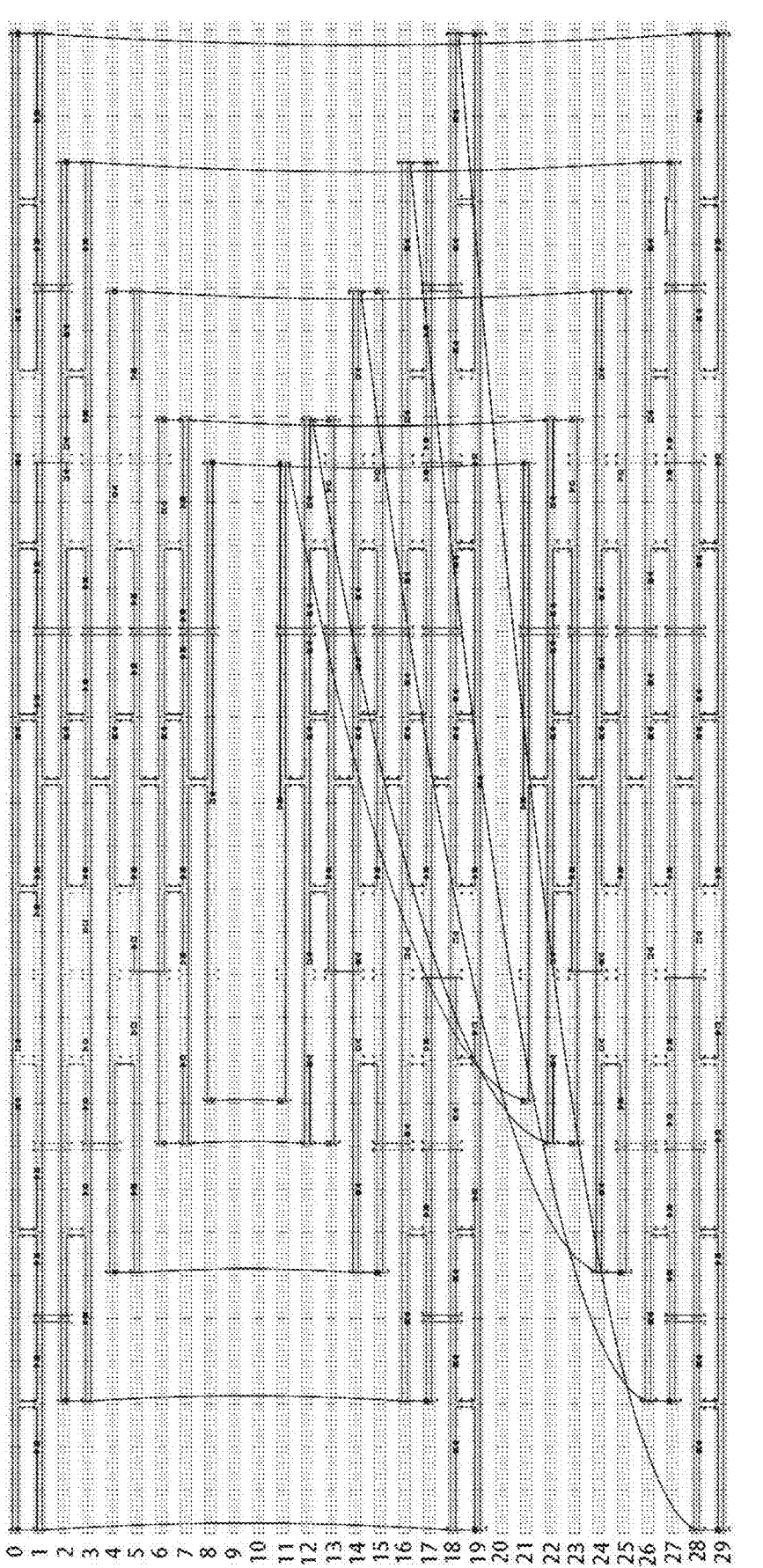
FIG. 1 is a design diagram of caDNAno software of the present disclosure, including respective block units of DNA triangular origami and staple strands.

Referring to FIG. 1, according to complementary DNA base pairing principle, a series of DNA patterns drawn by repeatedly folding long single-stranded DNA with short single-stranded DNA designed by caDNAno software are called DNA origami. Natural long single-stranded DNA is called a DNA scaffold strand, and short single-stranded DNA is called a DNA staple strand.

According to Watson-Crick base-pairing rules, DNA origami is a series of DNA structures synthesized by repeatedly folding long single-stranded DNA with short single-stranded DNA designed by software. The long single-stranded DNA is called DNA scaffold, and the short single-stranded DNA is called DNA staples.

Embodiment 1

A preparation method of a double emulsion stabilized by a single emulsifier based on DNA triangular origami technology includes following specific steps.

(1) Refer to FIG. 1, respective block units of DNA triangular origami are designed in caDNAno software so as to obtain DNA staple strands at the same time, as shown in Table 1:

Cholesterol is modified onto 3' ends of the DNA staple strands in sequences of SEQ ID NO.2, SEQ ID NO.5, SEQ ID NO.6, SEQ ID NO.10, SEQ ID NO.13, SEQ ID NO.18, SEQ ID NO.19, SEQ ID NO.20, SEQ ID NO.24, SEQ ID NO.31, SEQ ID NO.36, SEQ ID NO.43, SEQ ID NO.47, SEQ ID NO.54, SEQ ID NO.57, SEQ ID NO.62, SEQ ID NO.63, SEQ ID NO.65, SEQ ID NO.66, SEQ ID NO.67, SEQ ID NO.68, SEQ ID NO.72, SEQ ID NO.77, SEQ ID NO.78, SEQ ID NO.82, SEQ ID NO.83, SEQ ID NO.87, SEQ ID NO.97, SEQ ID NO.99, SEQ ID NO.105, SEQ ID NO.111, SEQ ID NO.112, SEQ ID NO.116, SEQ ID NO.119, SEQ ID NO.126, SEQ ID NO.129, SEQ ID NO.135, SEQ ID NO.136, SEQ ID NO.139, SEQ ID NO.141, SEQ ID NO.142, SEQ ID NO.145, SEQ ID NO.149 and SEQ ID NO.155.

(2) 10 nM of DNA scaffold strand M13mp18 and 100 nM of the DNA staple strands are solved in a TAE-Mg2+ buffer.

(3) The mixed DNA scaffold strand and DNA staple strands are placed in a PCR instrument, the temperature program is set to be 95° C. for 3 min followed by temperature drops from 95° C. to 15° C. at a cooling rate of 0.01° C./s. The DNA triangular origami was purified and enriched to 10 μM by an ultrafiltration tube.

(4) 500 μg/mL arbutin and 100 μg/mL coumaric acid were added into an internal water phase and oil phase respectively, and the internal water phase contains 10 μM of the DNA triangular origami. 3 mL of the internal water phase is added into 15 mL of the oil phase, and ultrasonic treatment is performed with ultrasonic power of 80 W, a frequency of 25 kHz and an ultrasonic duration of 90 s (operating for 1 s and stopping for 1 s) to obtain a W/O emulsion.

(5) 3 ml of the W/O emulsion is taken to add into 15 mL of an external water phase containing 100 μM of the DNA triangular origami, and ultrasonic treatment is performed with ultrasonic power of 80 W, a frequency of 25 kHz and an ultrasonic duration of 90 s (operating for 1 s and stopping for 1 s) to obtain a W/O/W double emulsion.

TABLE 1

| No. | Sequence (5' to 3') | length (nt) | Modification |
|---|---|---|---|
| 1 | GCCTGAGTGCATAAAGCTAAATCGTTCATTTGGGGCGCG ATATAATGC | 48 | |
| 2 | GCAAACAAGAGAATCGATGAACGGGTAGCTATTTTTGAG AAATGCAAT | 48 | 3'Cholesterol |
| 3 | CACCCTCAGCCGGTTTATCAGCTTGCTCTCCAAAA | 35 | |
| 4 | GTAAAGCCTGGGGTGCTTTATTTCAACGCAAG | 32 | |
| 5 | AAATATCGCGTAACAGTTCAGAAAACGACACTATC | 35 | 3'Cholesterol |
| 6 | TTAGTTTGCCATATAACAGTTGATTCCCAATT | 32 | 3'Cholesterol |
| 7 | TAAATCCTAAGCGTCATACATGGCTTTTGATGATA | 35 | |
| 8 | AATCAGATTCCTGAATCTTACCAACGCTAACGAGCGTCT T | 40 | |
| 9 | GGTAATAGTAATCATACAGGCAAGGCAAAAGG | 32 | |
| 10 | GATAGCGTCCAATAAGAAGTTTTGCCAGATAATAA | 35 | 3'Cholesterol |
| 11 | ATTATTACGAGAGGCTTTTGCAAACTGCGGAATCG | 35 | |
| 12 | CACTTGAAACATGAAAGTATTAAGAGGCTGAGACTCAA G | 39 | |
| 13 | GGTGGTTCCGAAATCGGCAAAATCCAGCAGGC | 32 | 3'Cholesterol |
| 14 | TTAATAGAAGGCTTATCCGTCGGCTGTCTTTC | 32 | |
| 15 | TCAGAGGGCGCATTAGACG | 19 | |
| 16 | GAATTGAGTGGGCGCATCGTAACCGTGCAAGC | 32 | |
| 17 | TCAGAACCGCCACCCTCCAGTACAAACTATCC | 32 | |
| 18 | TCATAATCAAAAGAGGCAGGTCAGACGAGTGTACTGGTA ATAAGTT | 46 | 3'Cholesterol |
| 19 | CTAATGAGTGAGCTAACCACGCTG | 24 | 3'Cholesterol |

TABLE 1-continued

DNA staple strands

| No. | Sequence (5′ to 3′) | length (nt) | Modification |
|---|---|---|---|
| 20 | GATAAAAATTTTTAGATATGACCCTGTAATACCGCAAATG GTC | 43 | 3′Cholesterol |
| 21 | CAAAAGAATATAATAACGGAATACCCAAACAC | 32 | |
| 22 | GCCTGTTTATCAAAGAAACCAATCAATAAGTATTC | 35 | |
| 23 | GGATTAGCGGGGTTTTTCAGAGCCACCACCCTCTA | 35 | |
| 24 | GAAAGACAGTTGTCACAATCAATAGAAAAATC | 32 | 3′Cholesterol |
| 25 | GGTAACGCCAGGGTTTTCCCAGTCTCCACACAACATACG ATGCG | 44 | |
| 26 | TCATAAGCAAACTCCAACAGGTCAGGATTAGAGAGTCTG | 39 | |
| 27 | CAAGGCGATTAAGTTGTGCCTGAGAGTCTGGA | 32 | |
| 28 | AAAACCAAAATAGCAGGTAGAAAGATTCAGTGAAT | 35 | |
| 29 | CCAGTTACAAAATAAAATTAACTG | 24 | |
| 30 | GTAGGAATCATTACCGCGCCCAATGTATTAAA | 32 | |
| 31 | CCAAGTACATTCTGTCCAG | 19 | 3′Cholesterol |
| 32 | TTTTTGTTTAAGCCTTAAATCAAGATAGGCGTTTT | 35 | |
| 33 | TAGAAAATACATACATAAAGGTGGCAACATATGCGCCAA AGACAA | 45 | |
| 34 | TTTCGTCACAGAGCCACCACCCTCAGAGCATG | 32 | |
| 35 | GGGAAGGTAAATATTGTCCAGAGCCTAATTTG | 32 | |
| 36 | CTTTTCAGCTAATGCAGAAAAATTCTTACCAGTAT | 35 | 3′Cholesterol |
| 37 | AAAGCCAACGCTCAACGACAATAAACAACATGATC | 35 | |
| 38 | GATTTAGGCGTTTACCAGACG | 21 | 3′Cholesterol |
| 39 | CTTGAGATGGTTTAATTTCAACTTTAATCATTTCAGTTGA | 40 | |
| 40 | TACAATTGCGAATAATAATTAGTTAGCGTAAC | 32 | |
| 41 | GTGTAGGTAAAGAATTAATGCCGGAGAGGTAATCG | 35 | |
| 42 | TAAAACTAGCTAAATTGTAAACGTTAATATTTTGTTAAAA TT | 42 | |
| 43 | GATCATTTTCAGGGATAGCCTCAAGAGAAGGATTA | 35 | 3′Cholesterol |
| 44 | AGGCGCATGACCAAC | 15 | |
| 45 | TTTGAAAGAGGACAGACATTAAACGGGTAAAA | 32 | |
| 46 | TTTCACCATTAATGAATCGGCCAATCATGGTCATA | 35 | |
| 47 | TCAAAAATGCTGCGCAACTGTTGGGAAGGCGA | 32 | 3′Cholesterol |
| 48 | GAATTACGAGGCATAGTAAGAGCAAGAATGAC | 32 | |
| 49 | GTGAGAAGAATTAGCAAAATTAACAATTCTACTAA | 35 | |
| 50 | TAAATCAGCTCATTTTTGTGAGCGAGTAACAACCCGTCG G | 40 | |
| 51 | TCAAAAATAATTCGCGTTAGCCGGAACGAGAC | 32 | |
| 52 | TTTAATTGCTCCTTTTGATAAGAGGTCATAGT | 32 | |
| 53 | CCTAAAACGAAAGGGTAGCAACGGCTACAGATCGT | 35 | |
| 54 | ATTCCAAGAACGGAGCAAGCA | 21 | 3′Cholesterol |

TABLE 1-continued

| No. | Sequence (5′ to 3′) | length (nt) | Modification |
|---|---|---|---|
| 55 | CCATAATTAGAGCCAGCAAATTCATATGGTTTA | 33 | |
| 56 | CCCAATAGGAACCCCACAGACAGCCCTCATTTTTC | 35 | |
| 57 | CGGTTGATAATCAGAAAATATTCATTACCGAC | 32 | 3′Cholesterol |
| 58 | ACGGAAATTATTCATTAAAGGTGATCAAGTTTGCCTTTAGCTTT | 44 | |
| 59 | GTTTGCCCCCTTATAAATCAAAGAATAGCCCGAGATAGGAGTTGCAG | 48 | |
| 60 | GCTGTTGCATGCCTGCAGGTGCGATCGGTGCGG | 33 | |
| 61 | GAAAATCCTGTTTGATCTGCGAACGAGTAGAT | 32 | |
| 62 | CCAAAAAGAAACGCAAAGAAGAACTGGCATGA | 32 | 3′Cholesterol |
| 63 | AATACGACGTTGTAAAACGAGCTGGCGAAAGGGGGATGTGCTG | 43 | 3′Cholesterol |
| 64 | AGATTAAGCCCAATAATAAGAGCAAGAAACAATCA | 35 | |
| 65 | CAGTTTCAGCGGAGTGAGAATAGATTTCCAGACGTTAGTACTCAG | 45 | 3′Cholesterol |
| 66 | CAAGCGGTCTCACATTAATTGCGTGCCGGAAGCATAAAGT | 40 | 3′Cholesterol |
| 67 | ACCAGTAGCACCATTACCTTTAATTGTATAGC | 32 | 3′Cholesterol |
| 68 | TCGGTCATAGCCCCCTCAAACAAA | 24 | 3′Cholesterol |
| 69 | AGTATGTTAGCAAACGAACACCCTGAACAAAG | 32 | |
| 70 | CCCCCTGCCTATTTCGGAACCTATTATTCGAG | 32 | |
| 71 | AAGACTTGAGCCATTTGGGCGATAGCAGCACCGTACAC | 38 | |
| 72 | ACCAATAGGAACGTGTATAAGCAAATATTATGTCA | 35 | 3′Cholesterol |
| 73 | ATCATATGTACCGTTCTAGCTGATAATTCAAAAGG | 35 | |
| 74 | AATATGAAATAGCAATAGCTATCTTACCGAAGCCCT | 36 | |
| 75 | TGAACGGTACGAGAAACACCAGAA | 24 | |
| 76 | ATGAGGGCTTGCAGGGAGTTATTAAACAGCTTGA | 34 | |
| 77 | CAGAAGCAAAGCGGATTGCATCAAAAAGATTAAAAAATCAGGTCTTTA | 48 | 3′Cholesterol |
| 78 | CACCGGAACCGCCACCAGAGCCGCCGCCAGCCTTG | 35 | 3′Cholesterol |
| 79 | GTAACAACATCAAGAGTAATCTTGGCGCAGACGGT | 35 | |
| 80 | GCCTCAGGAAGATCGCCGCATTAAATTTTTGT | 32 | |
| 81 | AGTAACAGTGCCCGTATAAACAGTTACGCCACCAG | 35 | |
| 82 | CTCTAGAGGATCCCCGGGGGAGGTTTTGAACG | 32 | 3′Cholesterol |
| 83 | AAAAGGCCAACGCCTGTAGCATTCATGTACCGTAA | 35 | 3′Cholesterol |
| 84 | AAGAAAAATTGCGTATTGGGCGCCAGGGTGGG | 32 | |
| 85 | GGAGATTTGTATCATCGCCTGATAAATTGTGTCAT | 35 | |
| 86 | GCCTTCCTGTAGCCAGCTTTCATCAACATTAAATTA | 36 | |
| 87 | AATAAGACATAAAAACAGGGAAGTAATTGAGCGCT | 35 | 3′Cholesterol |
| 88 | AACCACCTCCCTCAGAGCCGCCATCACCAATGAAA | 35 | |
| 89 | CCGGAGACAGTCAAATCAAAAATCTACGTGGG | 32 | |

TABLE 1-continued

| No. | Sequence (5′ to 3′) | length (nt) | Modification |
|---|---|---|---|
| 90 | CAATCGAAATCCGCGACCTGCTCCATGTTACTCTG | 35 | |
| 91 | GTTTTCATCGGCATTTCGTTTTTATTTTCATC | 32 | |
| 92 | ACGTTGAAAATTTCGAGGTGAATTTCAAGGCCGCT | 35 | |
| 93 | ACTAAAGGCGATAGTTGCGCCGACAATGACAACAACCATC | 40 | |
| 94 | CGAAAAACCGTCTATCACATAATTACTAGAAC | 32 | |
| 95 | GGAACCAGAGCATCAGTAGCGACAGAAATTATCAC | 35 | |
| 96 | AACCGCCACCCGCTCAGTACCAGGCGGATAAGTGC | 35 | |
| 97 | AGTCTCTGAATTTACCGTTCCAGTCATTAAAG | 32 | 3′Cholesterol |
| 98 | TAAAGAACGTGGACTCCAACGTCAAAGGTTTTTCT | 35 | |
| 99 | GAGAATATAAAGTACCCAACGCCAACATGTAATTTAGGCAGAGGCATT | 48 | 3′Cholesterol |
| 100 | CCAGAATGGAAAGCGCTTCGAGCCAGTAATAA | 32 | |
| 101 | TACATAACGCCAAAAGGCTAAACAACTTTCAA | 32 | |
| 102 | CGTCGAGACCTCAGAACCGCCACCAATGAATTTTCGGGATTTT | 43 | |
| 103 | GCCACGGCCAGTGCCAAGCTTTCCTGTGTGAAATTCTG | 38 | |
| 104 | TTACGAACAAAGTTACCAGAAGGAAACCGAGGAAA | 35 | |
| 105 | CTCACTGCCCGCCGCCTGGCCCTGAGAGGTTGAGT | 35 | 3′Cholesterol |
| 106 | AAGAACCGGAGCCCCAAAAACAGGAAGATCCA | 32 | |
| 107 | ATATTGTTGTACCAAAAACATACCCTCAT | 29 | |
| 108 | CCGACTTGCGTACCGAGCTCGAATTCGTAACG | 32 | |
| 109 | ATATTTTAGATCTACAAAGGCTATCAGGTCAT | 32 | |
| 110 | TTTTAAGAAAAGTAAGCAGATAGCAGACTCCTTATTACGC | 40 | |
| 111 | GGTTTAGTACCGCCACGGGTTGATATAAGTATAGCCCGGAATAGGTGT | 48 | 3′Cholesterol |
| 112 | TGTAGCTCAACATGTTTTAAATATCCTGTTTAGCT | 35 | 3′Cholesterol |
| 113 | GCCATTCGCCATTCAGGAAAATAGCAGCCCAA | 32 | |
| 114 | TCATTCAGTGGATTTTAAGAACTGGCCGGAACAAC | 35 | |
| 115 | AGCATTAACATCCAATAAAAATGTTTAGAACC | 32 | |
| 116 | AAGCGAACCAGACCGGAAATATTCATTGAATCATA | 35 | 3′Cholesterol |
| 117 | GTAAAGTACGCACTCATCGAGAACAAGCAAGC | 32 | |
| 118 | AATAAGCAACTAAAGTACGGTGTCTGGAAGTTTCATTACCATTAG | 45 | |
| 119 | GCCGCCGGAAACCAGGCAATCTGCCAGTTTGA | 32 | 3′Cholesterol |
| 120 | CACGGAATAAGTTTATTCATCGGAACGAGAGG | 32 | |
| 121 | CGAGTAGTAAATTGGGGCCCACGCATAACCGA | 32 | |
| 122 | AACGAACTAATCATTATACCAGTCAGCAAATCAAC | 35 | |
| 123 | TACCTTATGCAATAAGGCTTGCCCTGGTACAGACC | 35 | |

TABLE 1-continued

| No. | Sequence (5' to 3') | length (nt) | Modification |
|---|---|---|---|
| 124 | ACGCCCCTCAAATGCTTTATTTAATTCGAGCTTCA | 35 | |
| 125 | ATAACCCTAATACCACATTCAACTAATGCAGA | 32 | |
| 126 | AAGGGAACCGAACTAGGCTGGCTGACCTTAGCTGC | 35 | 3'Cholesterol |
| 127 | AAAAGGAGCCATTAGCAAGGCCGGAAACGCCC | 32 | |
| 128 | ACGACAGTAGGGCTTAATTGAGAATCGCCATATTTAAGA CAAAAG | 45 | |
| 129 | TCGTGCCAGCTGCAGTGAGACGGGCAACACACTAT | 35 | 3'Cholesterol |
| 130 | GTTGTTCCAGTTTGGAACAAGAGTCGCTGATTGCC | 35 | |
| 131 | ATTCTCCGTGGGAACAAACGGCGGGACGACGACAGTAT CG | 40 | |
| 132 | CCTGAAAAGCCTGTTTAGTATCATATGCGTTATACCGC | 39 | |
| 133 | TTAACGGGGTCAGTGCATTGACAGGAGGTTTCACC | 35 | |
| 134 | CGCAACACTAAAACACTCATCTTTGACCCCCACAA | 35 | |
| 135 | TTTGCGGGAGGCTTTGAGGACTAGCCACTACGAAG | 35 | 3'Cholesterol |
| 136 | TAGTTTTTGCGGATGGCTTAGAGCTTAATTGCT | 33 | 3'Cholesterol |
| 137 | CGCGGGGAGAGGCGGTTAATATCCCATCCCTC | 32 | |
| 138 | TAAGAACGCGTAGTTGCTATTTTGCACCCAATCCA | 35 | |
| 139 | AAGTTTTGTCGTCAAGGAACA | 21 | 3'Cholesterol |
| 140 | CTTCACTTTCCAGTCGGGAAACGTTATCCGCTCAC | 35 | |
| 141 | CGTCACCGGGCGACATTCAACCGATTGAGGGA | 32 | 3'Cholesterol |
| 142 | ATACATTTTTTGCGGGAGAAGCC | 24 | 3'Cholesterol |
| 143 | TACGTAATAAGACTTTTTC | 19 | |
| 144 | CATAAATCAGAGGAAGCCCGAAAGACTTC | 29 | |
| 145 | GTTGGGAAGACCATCAATATGATATTCAACCC | 32 | 3'Cholesterol |
| 146 | CCCTGACTATTATAGTATCACCGTACTCAGGA | 32 | |
| 147 | GGAGACAGCCATATTATTTATCCCAGCTACAATT | 34 | |
| 148 | GAGAGATAACCCATTTACAGAGAGAATAAAACGAT | 35 | |
| 149 | TTTGCCATCGTCAGACTGTAGCGC | 24 | 3'Cholesterol |
| 150 | GCACGCGATTATACCAAGCGCGAAACAAAGTACAAC | 36 | |
| 151 | ACTCCAGCCAGCTTTCCGGCACCGCTTCTGGTTCTTCGC TATTAC | 45 | |
| 152 | GGGATTGACCGTAATGGGATAGGTCACGTTGGTGT | 35 | |
| 153 | GAAGCTGAAAAGGTGGCATGCAATAAAGCCTCAGAAAT | 38 | |
| 154 | TATATTCGGTCGCTGAGAAGTTTC | 24 | |
| 155 | AGCGAACTAATTTACGAGCATGTCAATAGATAAGT | 35 | 3'Cholesterol |
| 156 | CAGGATTGGCCTTGATATTCATATTAGCG | 29 | |

Comparative Embodiment 1

All of conditions are the same as in Embodiment 1, except that a number of cholesterol-modified DNA staple strands in each of the block units in step (1) is 10.

Comparative Embodiment 2

All of conditions are the same as those in Embodiment 1, except that a concentration of the DNA triangular origami purified in step (3) is 5 μM.

Comparative Embodiment 3

All of conditions are the same as in Embodiment 1, except that:

In step (4), a commonly used O/W emulsifier Tween 80 is used to replace the DNA triangular origami, and in step (5), W/O PGPR is used to replace the DNA triangular origami. Quality indexes of above-mentioned products or products in intermediate steps are inspected specifically as follows.

The DNA triangular origami obtained by purification and enrichment in step (3) is inspected by an atomic force microscope, agarose gel electrophoresis and a contact angle tester.

Atomic force microscope (AFM) detection is as follows.

In this experiment, a mica substrate was used to fix the DNA triangular origami. The DNA triangular origami of Embodiment 1 was diluted 100 times, and 0.3 μL, of diluted samples were respectively adhered onto a mica sheet, standing for 5 min, washed with 100 μL, of ultrapure water, naturally air-dried and scanned under a Dimension Icon atomic force microscope, with a scanning mode of peak force tapping.

Agarose gel electrophoresis detection is as follows.

Agarose gel with a concentration of 0.8% was prepared with a 1×TAE-Mg2+ buffer, and the 1×TAE-Mg2+ buffer was added into an electrophoresis tank. 10 μL of the DNA triangular origami of Embodiment 1 was mixed with 2 μL of 6×Loading Buffer, injected into the gel hole, and electrophoresed at 100V for 60 min. After electrophoresis, it was stained with 4×SYBR Gold and imaged in a gel imager. A DNA structure represented by each of strips is determined according to a migration speed of the strip in an imaging map.

Interfacial tension test is as follows.

An oil phase is poured into a transparent glass dish and a water phase into a syringe. In Embodiment 1, 10 μM of the DNA triangular origami of Embodiment 1 is added into the water phase. In Comparative Embodiment 1 10 μM of the DNA triangular origami of Comparative Embodiment 1 is added into the water phase. In Comparative Embodiment 2 5 μM of the DNA origami of Comparative Embodiment 3 is added into the water phase. In Comparative Embodiment 3, 10 μM of Tween 80 is added in the water phase. Under action of gravity, water will form droplets in the oil phase. A CCD camera is used to record a change process of water droplets in the oil phase. An analysis software provided by the instrument is used to fit a Young-Laplace equation, and an interfacial tension value is obtained.

The W/O/W emulsion obtained in step (5) was tested for emulsion stability and release curves.

Emulsion stability analysis is as follows.

Turbiscan Lab Expert was used to measure emulsion stability. The W/O/W emulsion of Embodiment 1 contains 10 μM of the DNA origami of Embodiment 1 in both its internal and external water phases, The W/O/W emulsion of Comparative Embodiment 1 contains 10 μM of the DNA triangular origami of Comparative Embodiment 1 in both its internal and external water phases, the W/O/W emulsion of Comparative Embodiment 2 contains 5 μM of the DNA triangular origami of Comparative Embodiment 2 in both its internal and external water phases, and the W/O/W emulsion of Comparative Embodiment 3 contains 10 μM of PGPR in its oil phase and 10 μM of Tween 80 in its water phase. 18 mL of the prepared W/O/W emulsion is poured into a cylindrical glass test tube, scanned every 30 min minutes for 24 hours, with temperature being set at 25° C. Turbiscan stability index of the emulsion was determined with a backlight scattering mode. The smaller the stability index, the more stable the emulsion is.

In vitro release experiment is as follows.

The W/O/W emulsion of Embodiment 1 contains 10 μM of the DNA origami of Embodiment 1 in both its internal and external water phases, The W/O/W emulsion of Comparative Embodiment 1 contains 10 μM of the DNA triangular origami of Comparative Embodiment 1 in both its internal and external water phases, the W/O/W emulsion of Comparative Embodiment 2 contains 5 μM of the DNA triangular origami of Comparative Embodiment 2 in both its internal and external water phases, and the W/O/W emulsion of Comparative Embodiment 3 contains 10 μM of PGPR in its oil phase and 10 μM of Tween 80 in its water phase. To study the in vitro release, 1 mL of the prepared W/O/W emulsion was placed in PBS solution with a physiological pH=7.4. This mixture was shaken at 200 rpm and then centrifuged at different time intervals (4, 8, 12, 16, 20 and 24 hours). HPLC was used to evaluate the in vitro release curve.

In Vivo Whitening Experiment of Zebrafish

The W/O/W emulsion of Embodiment 1 contains 10 μM of the DNA origami of Embodiment 1 in both its internal and external water phases, The W/O/W emulsion of Comparative Embodiment 1 contains 10 μM of the DNA triangular origami of Comparative Embodiment 1 in both its internal and external water phases, the W/O/W emulsion of Comparative Embodiment 2 contains 5 μM of the DNA triangular origami of Comparative Embodiment 2 in both its internal and external water phases, and the W/O/W emulsion of Comparative Embodiment 3 contains 10 μM of PGPR in its oil phase and 10 μM of Tween 80 in its water phase. Wild AB zebrafish embryos were adopted for whitening experiment of zebrafish, and healthy zebrafish embryos cultured for 10 hours were used for emulsion intervention experiment. They were randomly divided into five groups, a blank control group (system water) and four treated groups (Embodiment 1, Comparative Embodiments 1 to 3), with 25 embryos in each group. The embryos in the treated group were cultured by mixing the zebrafish system water with the emulsion at a ratio of 1:1, with intervention of UV-B (312 nm) with intensity of 0.5 W/m$^2$ applied for 24 hours. After 62 hours of cultivation, zebrafish was anesthetized with tricaine, fixed on a slide with 3% methylcellulose solution, and placed under stereomicroscope to observe the whitening effect.

Determination of Melanin Content in Zebrafish

The W/O/W emulsion of Embodiment 1 contains 10 μM of the DNA origami of Embodiment 1 in both its internal and external water phases, The W/O/W emulsion of Comparative Embodiment 1 contains 10 μM of the DNA triangular origami of Comparative Embodiment 1 in both its internal and external water phases, the W/O/W emulsion of Comparative Embodiment 2 contains 5 μM of the DNA triangular origami of Comparative Embodiment 2 in both its internal and external water phases, and the W/O/W emulsion of Comparative Embodiment 3 contains 10 μM of PGPR in its oil phase and 10 μM of Tween 80 in its water phase. The above five groups of zebrafish embryos (blank group, Embodiment 1, Comparative Embodiments 1 to 3) are taken to measure the melanin content, with 15 embryos in each group. Sodium deoxycholate solution is added for ultrasonic crushing. After centrifugation at 3000 g for 5 minutes, precipitate was dissolved in 150 μL of 1 mol/L NaOH solution at 100° C. and vortexed for 10 minutes, then centrifuged at 3000 g for 5 minutes. Optical density (OD405) of supernatant of each group was measured at a wavelength of 405 nm. Relative melanin content of zebrafish in each group was calculated by taking the melanin content of the blank control group as 100%.

Results are as follows:

(1) AFM Characterization of DNA Triangular Origami

Figure 2:
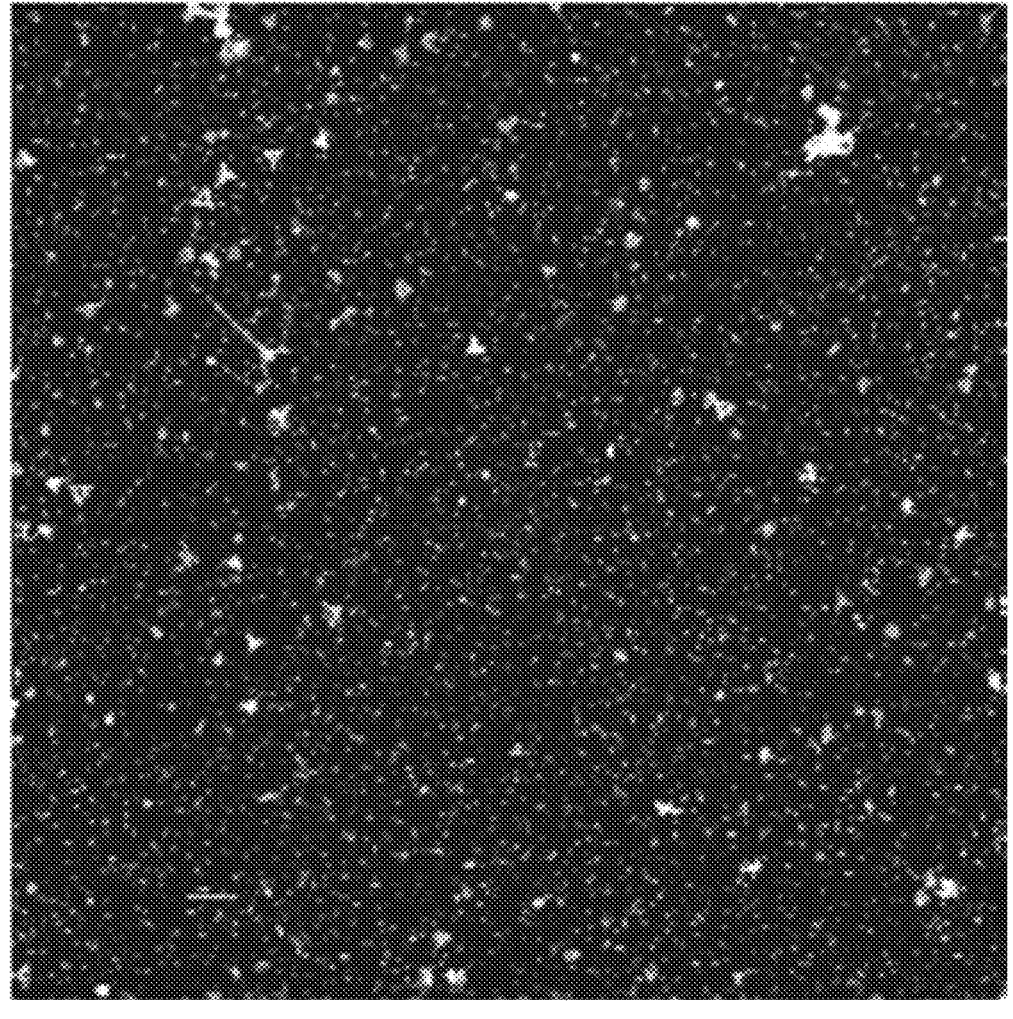
FIG. 2 shows an AFM image of DNA triangular origami.

As shown in FIG. 2, an AFM image shows that the DNA triangular origami has been successfully synthesized.

(2) Agarose Gel Electrophoresis

Figure 3:
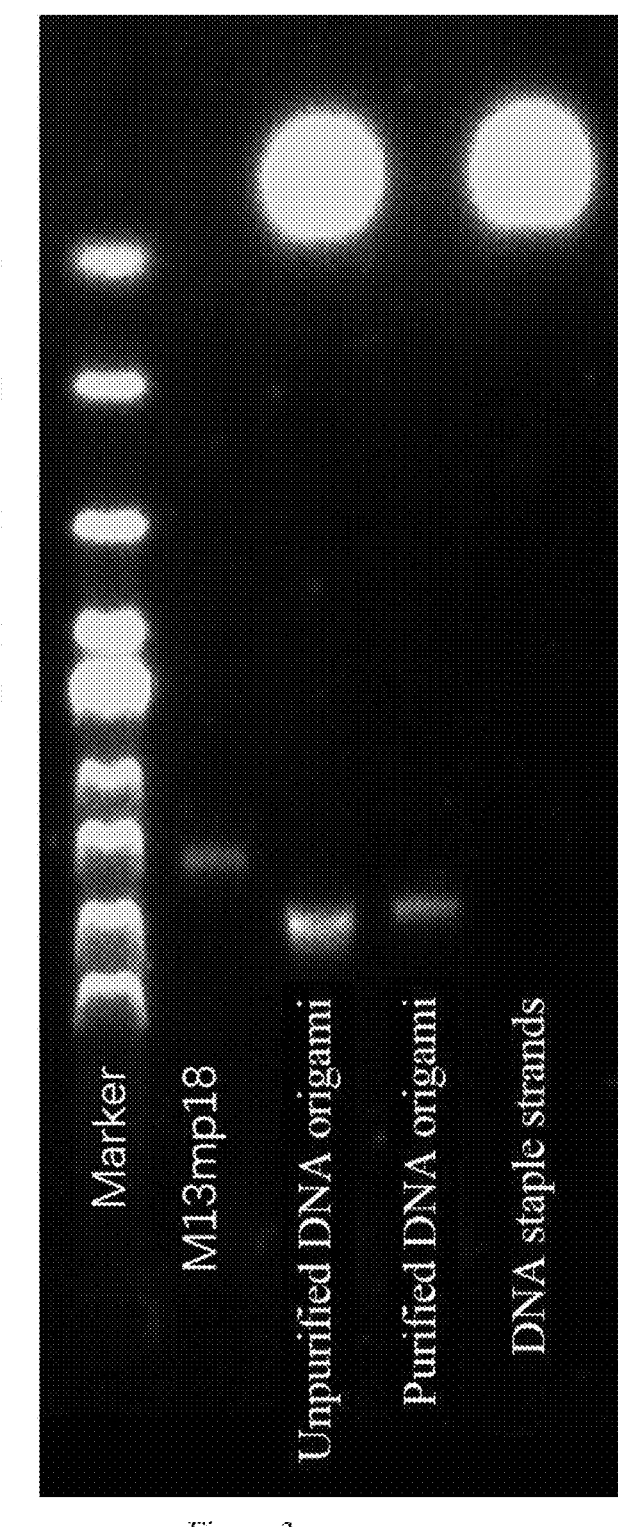
FIG. 3 is an agarose gel electrophoretogram.

As shown in FIG. 3, molecular weight of the DNA triangular origami after synthesis is higher than that of the scaffold strand M13mp18, which once again confirms successful synthesis of the DNA triangular origami. Redundant DNA staple strands are successfully removed by ultrafiltration.

(3) Interfacial Tension

As shown in Table 2, the DNA triangular origami prepared in Embodiment 1 can significantly reduce an interfacial tension of a water-oil interface, which is beneficial to stability of the water-oil interface. The effect of Embodiment 1 on reducing the interfacial tension between water and oil even exceeds that of commercial common emulsifiers Tween 80 and PGPR in Comparative Embodiment 3. But for Comparative Embodiment 1 and Comparative Embodiment 2, amount of modified cholesterol and the concentration of the DNA triangular origami were reduced, respectively, and decrease of interfacial tension was reduced, which indicates that it was not conducive to stability of the oil-water interface.

TABLE 2

Interfacial tensions for different water and oil phases

| Water phase | Oil phase | Interfacial tension (mN/m) |
|---|---|---|
| water | oil | 21.72 |
| Embodiment 1 | Embodiment 1 | 4.22 |
| Comparative Embodiment 1 | Comparative Embodiment 1 | 9.48 |
| Comparative Embodiment 2 | Comparative Embodiment 2 | 12.35 |
| Comparative Embodiment 3 | Comparative Embodiment 3 | 5.59 |

(4) Stability of W/O/W Double Emulsion

Figure 4:
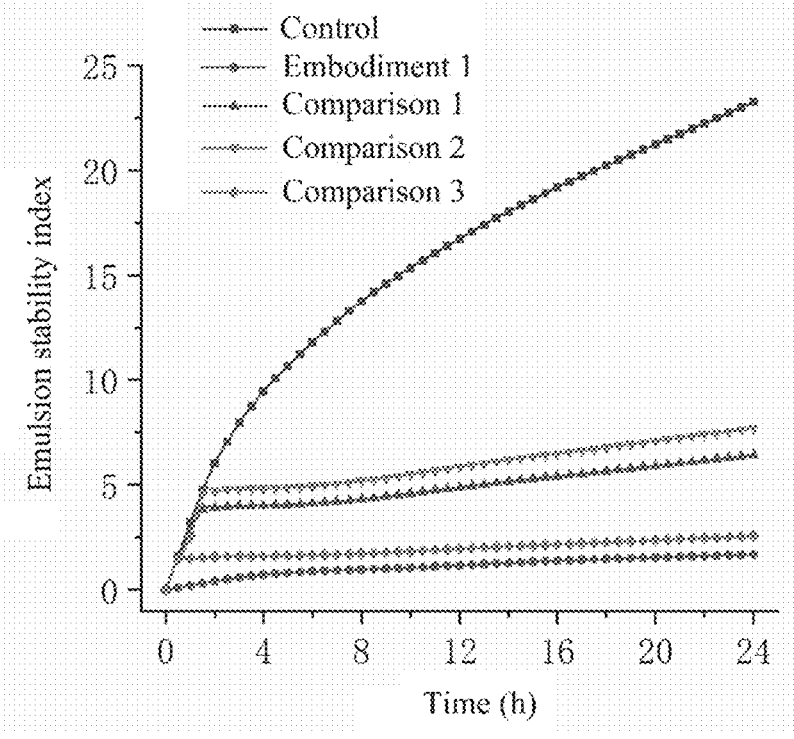
FIG. 4 is a stability analysis diagram of a W/O/W double emulsion.

As shown in FIG. 4, the blank control group contains a W/O/W double emulsion without any emulsifier, and its emulsion stability index is highest, indicating that the emulsion is unstable. In Embodiment 1, the emulsion stability index can be reduced to a greatest extent, and stability of the W/O/W double emulsion can be greatly improved, with better effect than that of the W/O/W double emulsion prepared using two conventional emulsifiers Tween 80 and PGPR in Comparative Embodiment 3. Emulsion stability indexes of Comparative Embodiment 1 and Comparative Embodiment 2 are relatively high, which indicates that emulsion stability for Comparative Embodiment 1 and Comparative Embodiment 3 is not high.

(5) Controlled Release of Arbutin and Coumaric Acid

Figure 5:
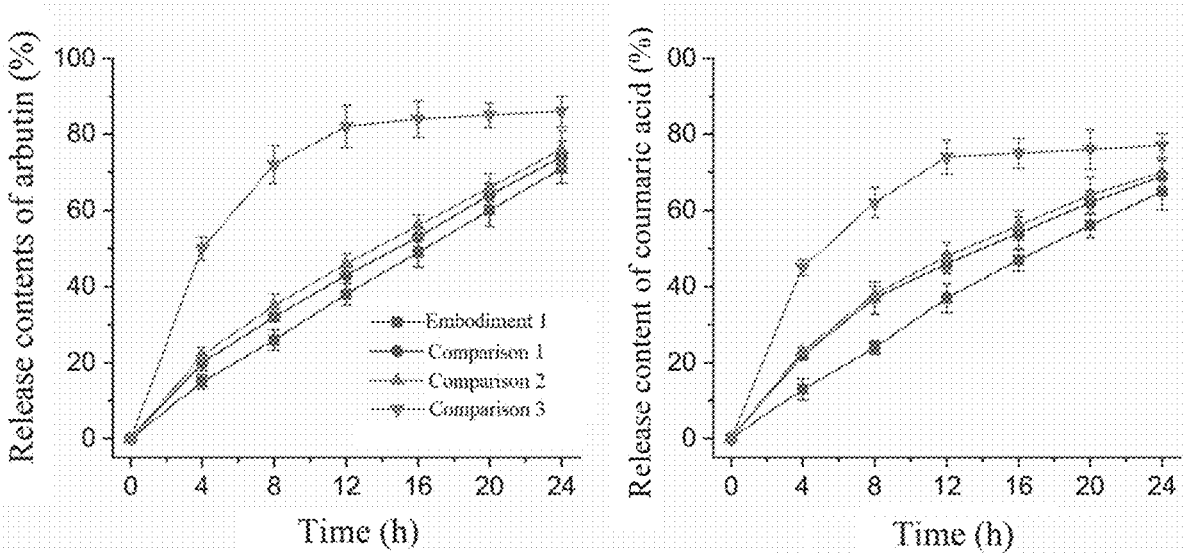
FIG. 5 shows release curves of arbutin and coumaric acid.

As shown in FIG. 5, zero-order release in a release process can be achieved for arbutin and coumaric acid in Embodiment 1, which facilitating sufficiently achieving whitening effect of arbutin and coumaric acid. The controlled release effect of arbutin and coumaric acid in Comparative Embodiments 1-3 is not achieved in an ideal state.

(6) Whitening Effect

Figure 6:
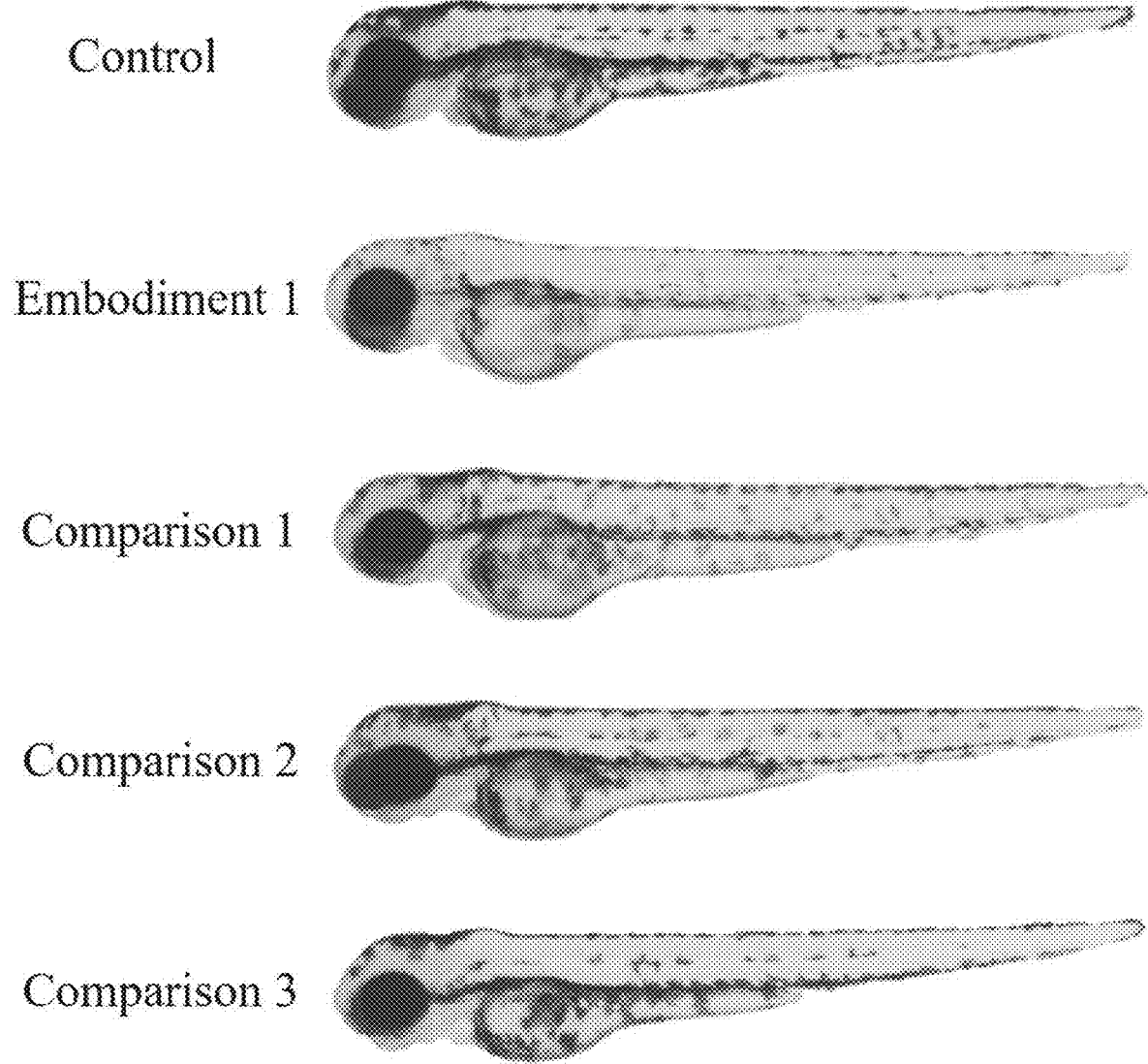
FIG. 6 shows whitening effect of zebrafish.
Figure 7:
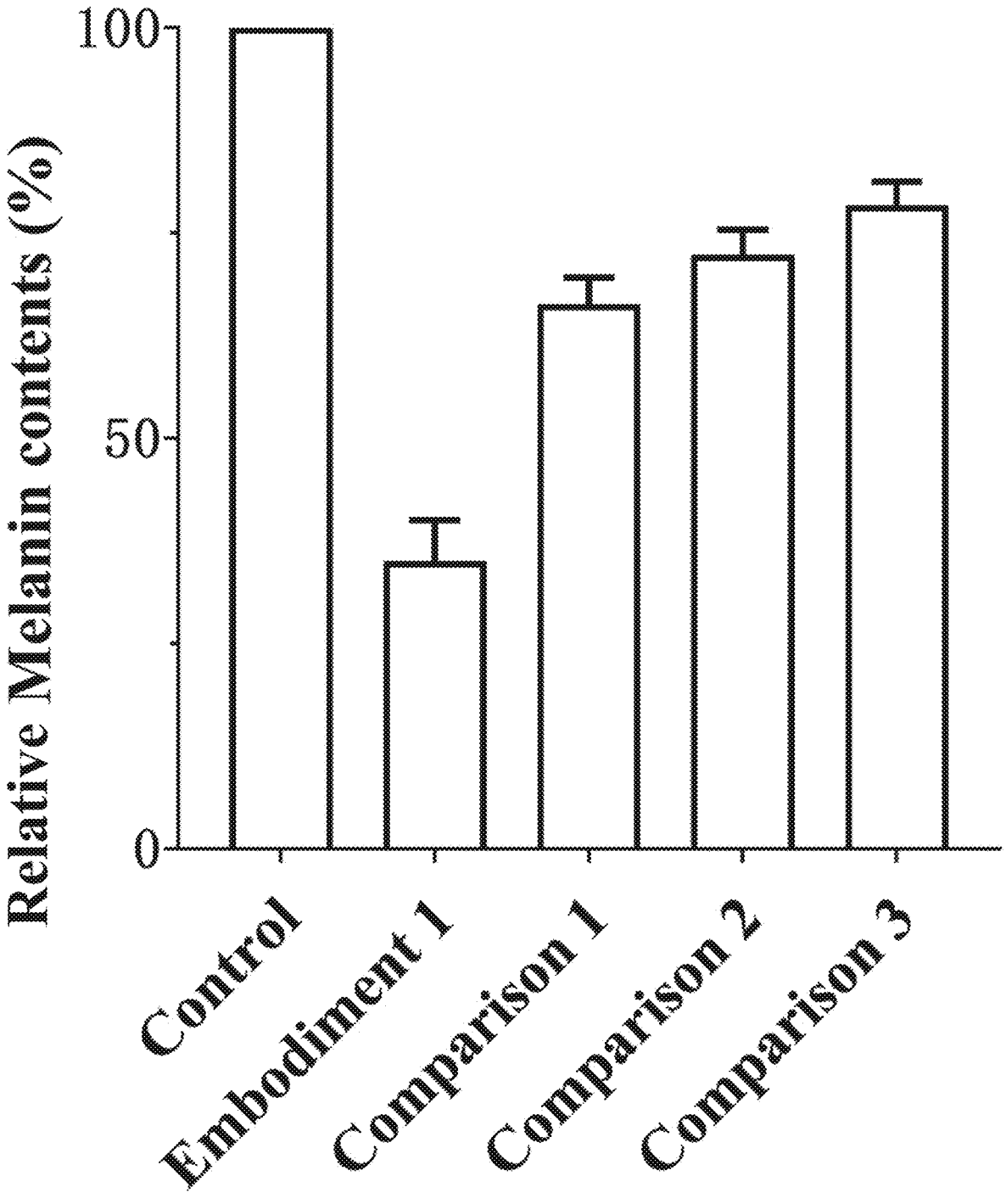
FIG. 7 shows melanin content of zebrafish.

As shown in FIG. 6 and FIG. 7, under intervention of UV-B, most significant whitening effect on zebrafish is achieved in Embodiment 1, the melanin content in zebrafish is reduced to the greatest extent. The whitening effect for both arbutin and coumaric acid in Comparative Embodiments 1-3 is not achieved in an ideal state, and the melanin content is not decreased significantly.

In the disclosure, the cholesterol is used to modify a specific number of DNA staple strands, and the prepared DNA triangular origami can be used as a single emulsifier to stabilize the W/O/W double emulsion, which has good stability and can simultaneously deliver hydrophilic arbutin and hydrophobic coumaric acid. The DNA triangular origami designed in the disclosure has the central nano hole, which can be used as a nano channel for release of arbutin and coumaric acid, thus controlling release of arbutin and coumaric acid, and having important significance in sufficiently achieving whitening effect of arbutin and coumaric acid.

The above is only preferred embodiments of the present disclosure, but not intended to limit the present disclosure in any form or substantially. It should be pointed out that some improvements and supplements can be made by those of ordinary skilled in the art without departing from methods of the present disclosure, which should also be regarded to be within a protection scope of the present disclosure. Some changes, modifications and equivalent changes can be made by any of technicians who are familiar with the art by using technical content disclosed above without departing from the spirit and scope of this disclosure, which are equivalent embodiments of this disclosure. Meanwhile, any alternations, modifications and evolutions to any equivalent change made to the above-mentioned embodiments according to essential technology of the present disclosure are still within the scope of technical schemes of the present disclosure.

The invention claimed is:

1. A single emulsifier based on DNA triangular origami technology, wherein the single emulsifier is DNA triangular origami prepared by modifying cholesterol onto DNA staple strands and then synthesizing with a DNA scaffold strand, the cholesterol being modified onto 3' ends of the DNA staple strands; and the DNA triangular origami has a central nano hole, both of the DNA triangular origami and the central nano hole are equilateral triangles, and a number of cholesterol-modified DNA staple strands in each block unit of the DNA triangular origami is 15;

wherein the cholesterol-modified DNA staple strands consist of SEQ ID NO.2, SEQ ID NO.5, SEQ ID NO.6, SEQ ID NO.10, SEQ ID NO.13, SEQ ID NO.18, SEQ ID NO.19, SEQ ID NO.20, SEQ ID NO.24, SEQ ID NO.31, SEQ ID NO.36, SEQ ID NO.43, SEQ ID NO.47, SEQ ID NO.54, SEQ ID NO.57, SEQ ID NO.62, SEQ ID NO.63, SEQ ID NO.65, SEQ ID NO.66, SEQ ID NO.67, SEQ ID NO.68, SEQ ID NO.72, SEQ ID NO.77, SEQ ID NO.78, SEQ ID NO.82, SEQ ID NO.83, SEQ ID NO.87, SEQ ID NO.97, SEQ ID NO.99, SEQ ID NO.105, SEQ ID NO.111, SEQ ID NO.112, SEQ ID NO.116, SEQ ID NO.119, SEQ ID NO.126, SEQ ID NO.129, SEQ ID NO.135, SEQ ID NO.136, SEQ ID NO.139, SEQ ID NO.141, SEQ ID NO.142, SEQ ID NO.145, SEQ ID NO.149 and SEQ ID NO.155.

2. A preparation method of a double emulsion based on DNA triangular origami technology, comprising following steps:

step (1): designing and synthesizing the DNA staple strands according to claim 1;

step (2): mixing and dissolving the DNA scaffold strand and the DNA staple strands in a buffer, and setting a temperature program to synthesize a DNA triangular origami;

step (3): purifying and enriching the DNA triangular origami obtained in step (2);

step (4): adding arbutin into an internal water phase, adding coumaric acid into an internal oil phase, adding the enriched DNA triangular origami obtained in step (3) into the internal water phase, which then is added into the internal oil phase and subjected to ultrasonic reaction to obtain a water-in-oil (W/O) emulsion; and step (5): adding the enriched DNA triangular origami obtained in step (3) into an external water phase, and then adding the W/O emulsion obtained in step (4) for ultrasonic reaction to prepare a water-in-oil-in-water (W/O/W) double emulsion based on the DNA triangular origami technology;

wherein in step (3), a concentration of the enriched DNA triangular origami is 10±1 µM.

3. The preparation method of the double emulsion based on the DNA triangular origami technology according to claim 2, wherein in step (1), a total number of the staple strands of the DNA triangular origami is 156.

4. The preparation method of the double emulsion based on the DNA triangular origami technology according to claim 2, wherein in step (2), the DNA scaffold strand is M13mp18, a molar concentration ratio of the DNA scaffold strand to the DNA staple strands is 1:10, and the buffer is a TAE-Mg2+ buffer, the temperature program is set to be 95° C. for 3 min, followed by temperature drops from 95° C. to 15° C. at a cooling rate of 0.01-0.02° C./s.

5. The preparation method of the double emulsion based on the DNA triangular origami technology according to claim 2, wherein in step (4), addition amount of arbutin is 500±1 µg/mL and addition amount of coumaric acid is 100±1 µg/mL.

6. The preparation method of the double emulsion based on the DNA triangular origami technology according to claim 2, wherein in step (4), a volume ratio of the internal water phase to the internal oil phase is 1:4 to 1:6, and in step (5), a volume ratio of the W/O emulsion to the external water phase is 1:4 to 1:6.

7. The preparation method of the double emulsion based on the DNA triangular origami technology according to claim 2, wherein in step (4) and step (5), ultrasonic power of the ultrasonic reaction is 80±5 W, with a frequency of 25±5 kHz and an ultrasonic duration of 90±5 s.

8. An operation method for a phenolic delivery system with the double emulsion based on the DNA triangular origami technology prepared by the method according to claim 2.

\* \* \* \* \*